(12) United States Patent
LaBeaume

(10) Patent No.: US 10,179,778 B2
(45) Date of Patent: Jan. 15, 2019

(54) SUBSTITUTED ARYL ONIUM MATERIALS

(71) Applicant: Rohm and Haas Electronic Materials LLC, Marlborough, MA (US)

(72) Inventor: Paul J. LaBeaume, Auburn, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 14/040,587

(22) Filed: Sep. 27, 2013

(65) Prior Publication Data

US 2015/0093708 A1    Apr. 2, 2015

(51) Int. Cl.
| | | |
|---|---|---|
| *C07D 409/10* | (2006.01) | |
| *G03F 7/004* | (2006.01) | |
| *C07C 381/12* | (2006.01) | |
| *C07D 333/76* | (2006.01) | |
| *C07J 31/00* | (2006.01) | |
| *C07D 335/16* | (2006.01) | |
| *C07C 323/62* | (2006.01) | |
| *C07J 9/00* | (2006.01) | |
| *G03F 7/038* | (2006.01) | |
| *G03F 7/039* | (2006.01) | |

(52) U.S. Cl.
CPC .......... *C07D 409/10* (2013.01); *C07C 323/62* (2013.01); *C07C 381/12* (2013.01); *C07D 333/76* (2013.01); *C07D 335/16* (2013.01); *C07J 9/005* (2013.01); *C07J 31/006* (2013.01); *G03F 7/0045* (2013.01); *G03F 7/0046* (2013.01); *G03F 7/0382* (2013.01); *G03F 7/0397* (2013.01)

(58) Field of Classification Search
CPC ....... C07C 381/12; G03F 7/004; G03F 7/027; G03F 7/028; G03F 7/20; C07D 409/10
USPC ..... 430/270.1, 322, 921, 922, 923; 560/8, 9; 568/77
See application file for complete search history.

(56) References Cited

U.S. PATENT DOCUMENTS

| | | | |
|---|---|---|---|
| 4,287,355 A | 9/1981 | Kathawala | |
| 8,318,403 B2 | 11/2012 | Ichikawa et al. | |
| 2003/0224285 A1* | 12/2003 | Nakao | G03F 7/0045 430/270.1 |
| 2004/0197707 A1* | 10/2004 | Yamanaka | G03F 7/0045 430/281.1 |
| 2007/0148592 A1* | 6/2007 | Wada et al. | 430/270.1 |
| 2007/0224540 A1* | 9/2007 | Kamimura | G03F 7/0045 430/270.1 |
| 2010/0063232 A1* | 3/2010 | Nagai et al. | 526/287 |
| 2012/0015299 A1 | 1/2012 | Komuro et al. | |
| 2014/0080056 A1 | 3/2014 | LaBeaume | |
| 2014/0080059 A1 | 3/2014 | LaBeaume et al. | |
| 2015/0093709 A1 | 4/2015 | LaBeaume | |
| 2016/0168117 A1 | 6/2016 | Labeaume | |

FOREIGN PATENT DOCUMENTS

| | | | |
|---|---|---|---|
| JP | 2004-361577 | * | 12/2004 |
| JP | 2004-361577 A | | 12/2004 |

OTHER PUBLICATIONS

Machine translation of JP 2004-361577, published on Dec. 24, 2004.*
Gupta, M, Vithayathil, P.—Isolation and Characterization of a Methionine Adduct of DOPA o-Quinone, Bioorganic Chemistry, 11, pp. 101-107, 1982.*
English Language Summary of Office Action and Search Report of Counterpart Taiwan Application No. 104-2(6) 01146-10420727600, dated Jun. 2, 2015—6 Pages.
English Language Summary of Taiwan Office Action dated Jul. 19, 2016, issued in counterpart Taiwan Application No. 105-2(6)01146-10520882710 (4 Pages).
Taiwan Office Action dated Jul. 19, 2016 issued in connection with Taiwanese counterpart application 103133462.

* cited by examiner

*Primary Examiner* — Anca Eoff
(74) *Attorney, Agent, or Firm* — Mintz Levin Cohn Ferris Glovsky and Popeo, P.C.; Peter F. Corless

(57) ABSTRACT

Acid generators comprising a carbocyclic or heteroaromatic group substituted with at least one diester moiety are provided. These acid generators are particularly useful as a photoresist composition component.

26 Claims, No Drawings

SUBSTITUTED ARYL ONIUM MATERIALS

FIELD

In one aspect, the present invention relates to new onium acid generators that comprise a substituted carbocyclic, aryl, or heteroaromatic group.

INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Known photoresists can provide features having resolution and dimension sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See US 20070224540 and EP 1906241. See also U.S. Pat. No. 8,318,403 and US 2012/0015299. Short-wavelength imaging also has been utilized, such as 193 nm. Extreme ultraviolet (EUV) and e-beam imaging technologies also have been employed. See U.S. Pat. No. 7,459,260. EUV utilizes short wavelength radiation, typically between 1 nm to 40 nm, with 13.5 nm radiation often employed.

EUV photoresist development continues to be a challenging issue for EUV Lithography (EUVL) technology implementation. Required are development of materials that can provided highly resolved fine features, including low linewidth roughness (LWR), and sufficient sensitivity to afford wafer throughput.

SUMMARY

We have now discovered new acid generators and photoresist compositions that comprise one or more of such acid generators.

In one aspect, acid generators are provided that comprise a substituted carbocyclic, aryl, or heteroaromatic group.

Particularly preferred acid generators may comprise a diester moiety represented by a structure of the formula:

—Y—C(=O)O(CX'X")$_n$C(=O)OR in which Y is a linker comprising one or more carbon atoms (such as a substituted alkylene group), provided that Y has at least one non-hydrogen substituent;

n is a positive integer each X' and X" is independently a hydrogen or non-hydrogen substituent; and R is a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic.

In certain preferred aspects, the acid generator comprises a structure of Formula (I):

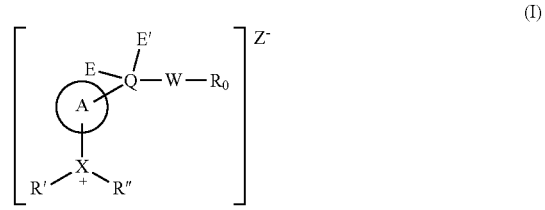

wherein Z is a counter anion, such as a non-nucleophilic anion (e.g., carboxylate, sulfate, sulfonate, sulfamate, or the anion of a sulfonamide or sulfonimide);

X is sulfur or iodine;

R$_0$ is hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic;

R' and R" are the same or different non-hydrogen substituents such as optionally substituted alkyl, optionally substituted heteroalkyl, optionally substituted alicyclic, optionally substituted heteroalicyclic, optionally substituted carbocyclic aryl or optionally substituted heteroaromatic, and optionally may form a ring, provided that if X is iodine, one of R' and R" is absent;

W is —O—, —S—, SO, SO$_2$, >CO, —O(C=O)—, —(C=O)O—, —N(C=O)—, —C=ON—, or —C(=O)O(CX'X")nC(=O)O—, wherein n is a positive integer and each X' and X" is independently a hydrogen or non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic;

A is optionally substituted carbocyclic aryl or optionally substituted heteroaromatic group (e.g., a C$_{6-14}$ carbocyclic aryl or optionally substituted heteroaromatic group having from 5 to 14 atoms, including 1-4 heteroatoms selected from O, S, and N, in the heteroaromatic ring system);

Q is optionally substituted C$_1$-C$_8$ alkylene, optionally substituted C$_1$-C$_8$ alkenylene, or optionally substituted C$_1$-C$_8$ alkynylene; and E and E' are each independently hydrogen or a non-hydrogen substituent, with at least one of E and E' being a non-hydrogen substituent.

In certain particularly preferred aspects of Formula (I), W is —(C=O)O— or —C(=O)O(CX'X")nC(=O)O—.

In certain embodiments of Formula (I), X is sulfur.

In certain preferred aspects, the acid generator comprises a structure of Formula (II):

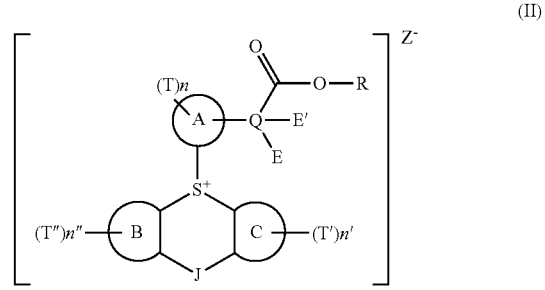

wherein Z is a counter anion, such as a non-nucleophilic anion (e.g., carboxylate, sulfate, sulfonate, sulfamate, or the anion of a sulfonamide or sulfonimide);

R is hydrogen or a non-hydrogen substituent;

each T, each T' and each T" are the same or different non-hydrogen substituent, wherein either of T and T" or T and T' are capable of joining to form a ring;

n is 0, 1, 2, 3 or 4;

n' and n" are each independently 0, 1, 2, 3, 4 or 5;

J represents a chemical bond, or a group capable of covalently linking B and C;

Q is a $C_1$-$C_8$ saturated or unsaturated alkylene group (which may be optionally substituted);

E and E' are each independently hydrogen or a non-hydrogen substituent, with at least one of E and E' being a non-hydrogen substituent; and A, B, and C are each the same or different carbocyclic aryl or heteroaromatic groups (e.g., $C_{6-14}$ carbocyclic aryl or heteroaromatic group having from 5 to 14 atoms, including 1-4 heteroatoms selected from O, S, and N, in the heteroaromatic ring system), each of which may be optionally substituted.

In certain preferred aspects, the present acid generators are onium compounds, such as iodonium or sulfonium materials, with sulfonium acid generators being generally preferred.

In certain preferred aspects, the acid generator comprises a structure of Formula (IIa):

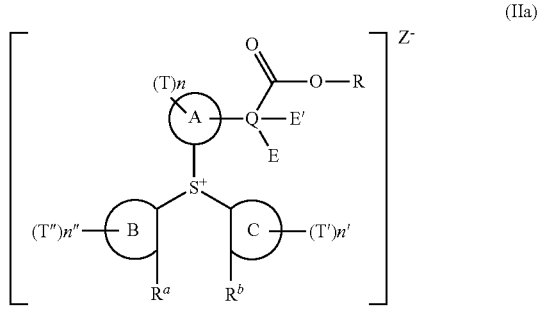

(IIa)

wherein Z is a counter anion;

R is hydrogen or a non-hydrogen substituent;

each T, each T' and each T" are the same or different non-hydrogen substituent, wherein either of T and T" or T and T' are capable of joining to form a ring;

n is 0, 1, 2, 3 or 4;

n' and n" are each independently 0, 1, 2, 3, 4 or 5;

$R^a$ and $R^b$ are each H, or $R^a$ and $R^b$ taken together represent a chemical bond or a group capable of covalently linking B and C;

Q is a $C_1$-$C_8$ saturated or unsaturated alkylene group;

E and E' are each independently hydrogen or a non-hydrogen substituent, with at least one of E and E' being a non-hydrogen substituent; and A, B, and C are each the same or different carbocyclic aryl or heteroaromatic groups.

Particularly preferred acid generators include those of the following Formula III:

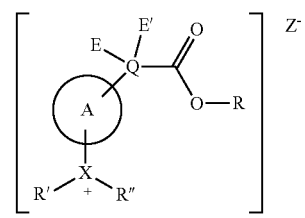

(III)

wherein E, E', Q, A, X, R', R" and $Z^-$ are as defined for Formula (I), and R is hydrogen or a non-hydrogen substituent.

Further preferred acid generators include those of the following Formula IV:

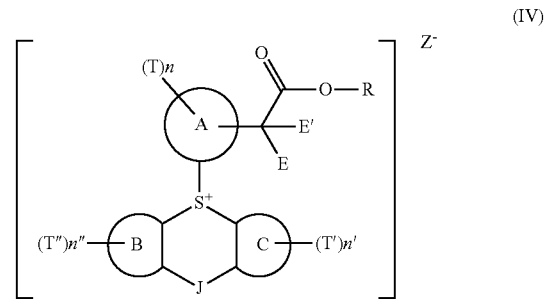

(IV)

wherein E, E', T, T', T", J, n, n', n" and $Z^-$ are as defined for Formula (II); A, B, and C are each the same or different carbocyclic aryl groups (e.g., $C_{6-14}$ carbocyclic aryl); and R is hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic.

Still further preferred acid generators include those of the following Formula V:

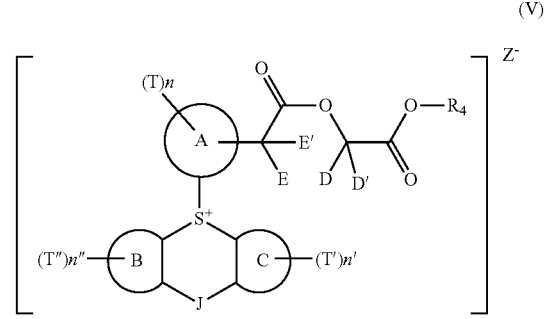

(V)

wherein E, E', T, T', T", A, B, C, J, n, n', n" and $Z^-$ are as defined for Formula (IV), D and D' are each hydrogen or a non-hydrogen substituent, including deuterium, and $R_4$ is an acid-labile group.

Preferred acid generators and photoresists of the invention are particularly useful for short-wavelength imaging, such as 193 nm and EUV imaging.

In preferred aspects, photoresist compositions are provided comprising (i) a polymer; (ii) an acid generator as disclosed herein.

In preferred aspects, the acid generators are acid-labile and react in the presence of acid during lithographic processing (exposure, post-exposure bake) of a photoresist coating layer containing the acid generator.

Preferred photoresists of the invention may comprise an imaging-effective amount of one, two or more acid generator compounds as disclosed herein and a suitable polymer component.

Methods are also provided for forming relief images of photoresist compositions of the invention (including patterned lines with sub sub-50 nm or sub-20 nm dimensions). Substrates such as a microelectronic wafer also are provided having coated thereon a photoresist composition of the invention.

DETAILED DESCRIPTION

As referred to herein, acid generators can produce an acid when exposed to activating radiation, such as EUV radiation, e-beam radiation or other radiation sources such as 193 nm wavelength radiation. Acid generators as referred to herein also may be referred to as photoacid generator compounds.

Acid Generators

As discussed above, in preferred aspects, ionic photoacid generators that comprise at least one diester moiety are provided, including compounds of Formula I-V above.

As used herein, the term "diester moiety" refers to a moiety having two ester moieties linked by a linking group:
—C(=O)O-L-C(=O)OR, in which L is a linking group.
Preferred diesters can be represented by a structure of the formula:

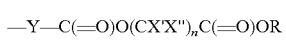

in which Y is a linker comprising one or more carbon atoms (such as a substituted alkylene group), provided that Y has at least one non-hydrogen substituent;

n is a positive integer each X and X' is independently a hydrogen or non-hydrogen substituent; and R is a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic.

Additional ionic photoacid generators that comprise at least one diester moiety including compounds represented by the following Formula VI:

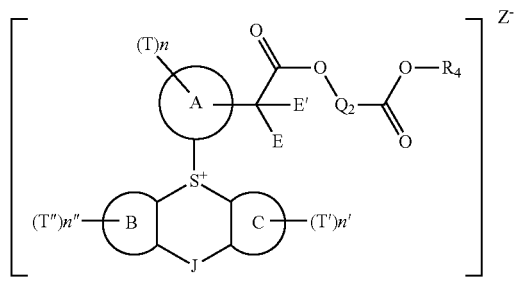

wherein
E, E', T, T', T", A, B, C, J, n, n', n", $R_4$ and $Z^-$ are as defined for Formula (V), and $Q_2$ is a $C_{1-8}$ alkylene group which may be fully or partially saturated and may be substituted with a carbonyl, oxygen, nitrogen, sulfur or any combination of carbonyl, oxygen, nitrogen, and sulfur; a carbocyclic aryl or heteroaromatic group (e.g., $C_{6-14}$ carbocyclic aryl or heteroaromatic group having from 5 to 14 atoms, including 1-4 heteroatoms selected from O, S, and N, in the heteroaromatic ring system); or a cycloalkyl group (e.g., a $C_{6-10}$ cycloalkyl group).

In the above Formulae (IV)-(VI), J suitably can be a single bond, optionally substituted alkylene group, C=O, O, S, SO, $SO_2$, NH, or NR (where R is a non-hydrogen substituent such as optionally substituted alkyl). J linker groups also may comprise various hetero groups and moieties such as ether, ester, amide, carbonate, sulfonate, sulfone, or sulfonamide, e.g. $CH_2$(C=O)—O—, $CH_2$(C=O)—OCH$_2$CH$_2$—, $CH_2$(C=O)—OCH$_2$CH$_2$O—, $CH_2$(C=O)—OCH$_2$—, $CH_2$(C=O)—OCH$_2$O—, —O—, —S—, —O—C(=O)—, —C(=O)—O—, —O—C(=O)—O—, —OCH$_2$—(C=O)O— or —OCH$_2$C(=O)—.

Additional ionic photoacid generators that comprise at least one diester moiety are provided, including compounds of the following Formula VII:

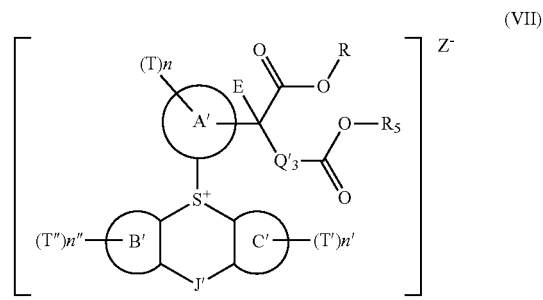

wherein

E, T, T', T", n, n', n", R and $Z^-$ are as defined for Formula (IV);

A', B', C' are each independently a $C_6$-$C_{36}$ aromatic, $C_5$-$C_{36}$ polyaromatic, or $C_5$-$C_{36}$ conjugated aromatic group;

J' represents no bond, a single chemical bond, or a group capable of covalently linking B' and C';

$R_5$ is hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic; and $Q'_3$ is a $C_{1-8}$ alkylene group which may be fully or partially saturated and may be substituted with a carbonyl, oxygen, nitrogen, sulfur or any combination of carbonyl, oxygen, nitrogen, and sulfur; a $C_1$ to $C_{30}$ aliphatic hydrocarbon group, a $C_1$ to $C_{30}$ cyclic hydrocarbon group (e.g., a $C_{6-10}$ cycloalkyl group), a $C_8$ to $C_{30}$ polycyclic hydrocarbon group, a $C_6$ to $C_{30}$ carbocyclic aryl or $C_5$ to $C_{30}$ heteroaromatic group (e.g., $C_{6-14}$ carbocyclic aryl or heteroaromatic group having from 5 to 14 atoms, including 1-4 heteroatoms selected from O, S, and N, in the heteroaromatic ring system).

Still further ionic photoacid generators that comprise at least one diester moiety include compounds of the following Formula VIII:

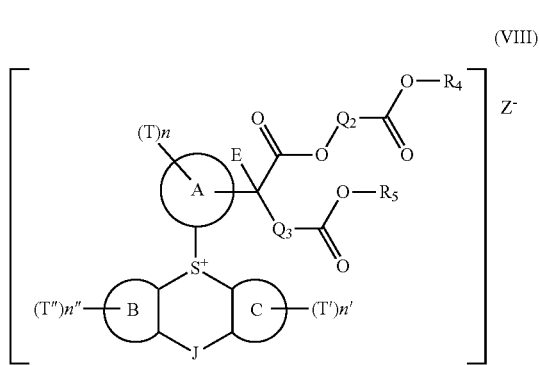

(VIII)

wherein

E, T, T', T", A, B, C, J, n, n', n", R and Z⁻ are as defined for Formula (IV);

$R_4$ and $R_5$ are each independently hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic; and $Q_2$ and $Q_3$ are each independently a $C_{1-8}$ alkylene group which may be fully or partially saturated and may be substituted with a carbonyl, oxygen, nitrogen, sulfur or any combination of carbonyl, oxygen, nitrogen, and sulfur; a carbocyclic aryl or heteroaromatic group (e.g., $C_{6-14}$ carbocyclic aryl or heteroaromatic group having from 5 to 14 atoms, including 1-4 heteroatoms selected from O, S, and N, in the heteroaromatic ring system); or a cycloalkyl group (e.g., a $C_{6-10}$ cycloalkyl group).

In certain embodiments, the counter anion Z is a carboxylate or sulfamate anion. In certain embodiments, the counter anion Z contains a polymerizable moiety.

Specifically preferred cations of ionic acid generators include the following:

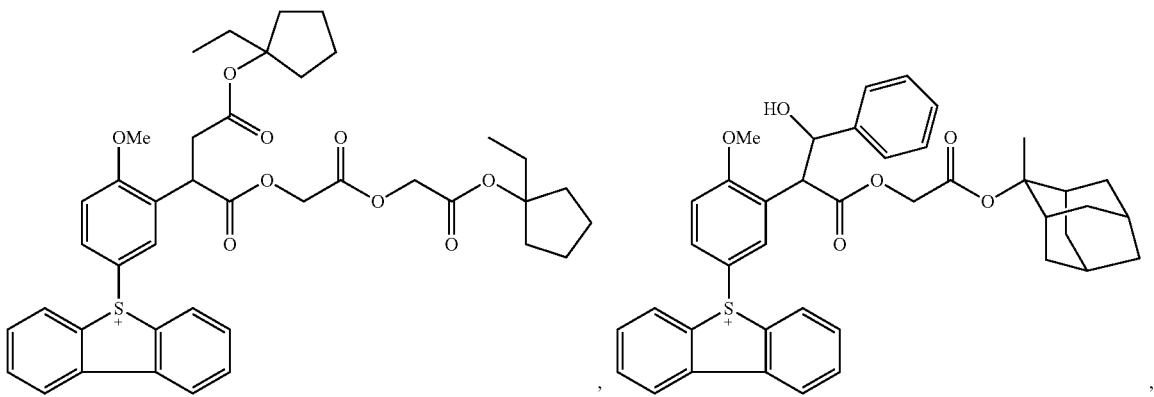

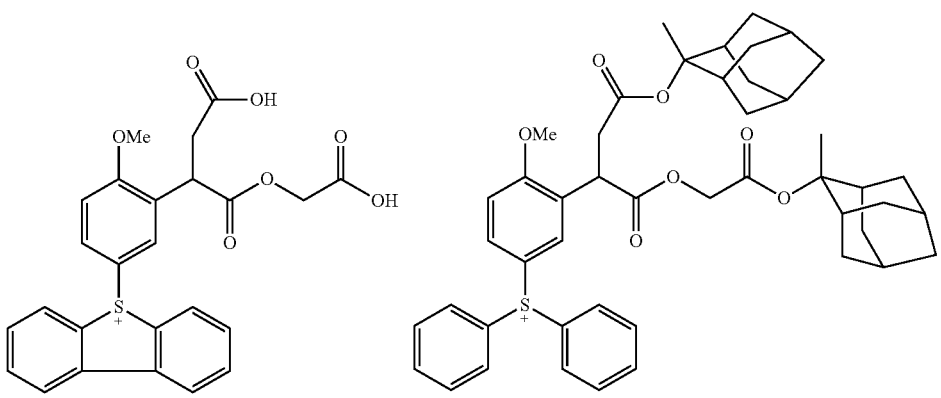

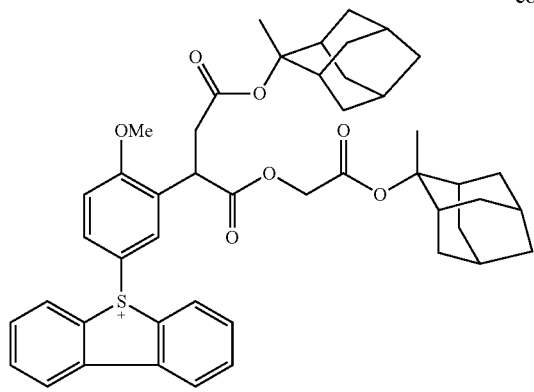
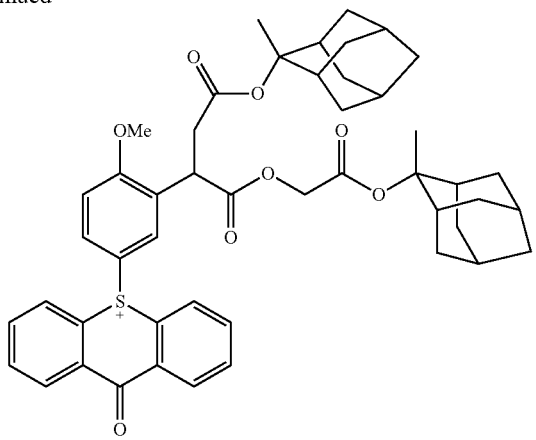
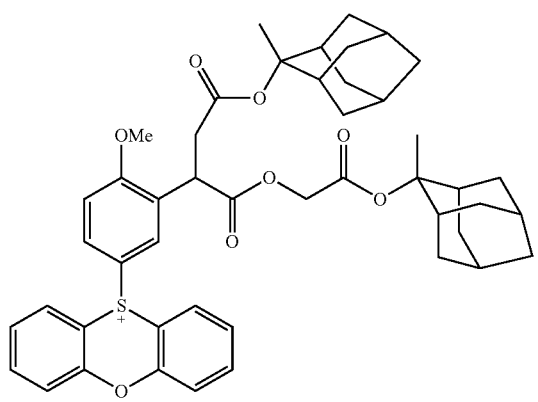
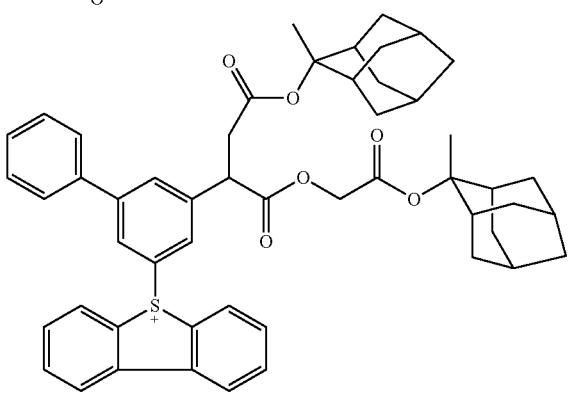
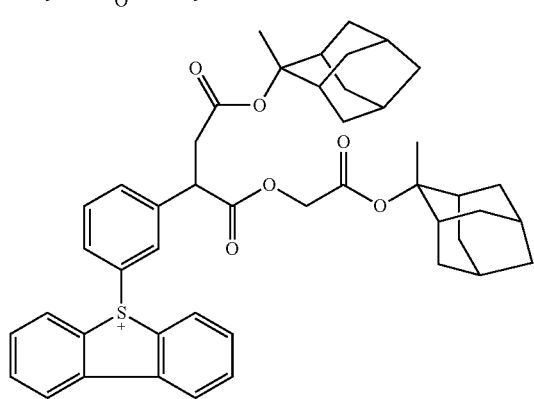
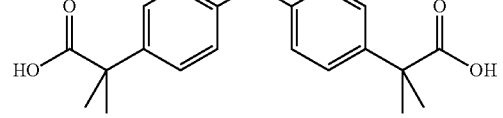
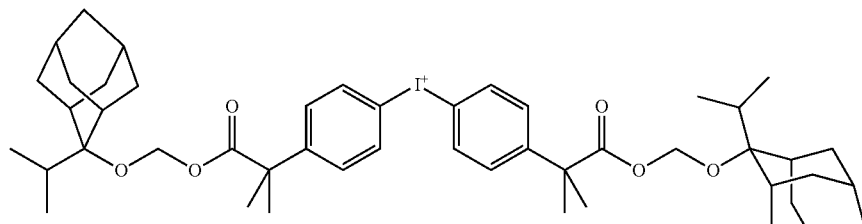
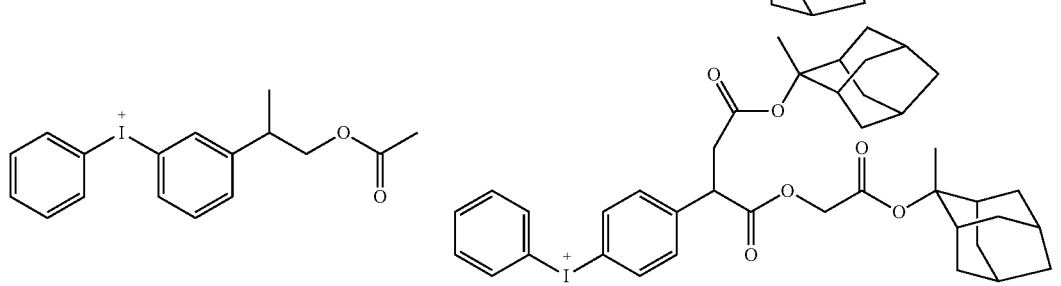

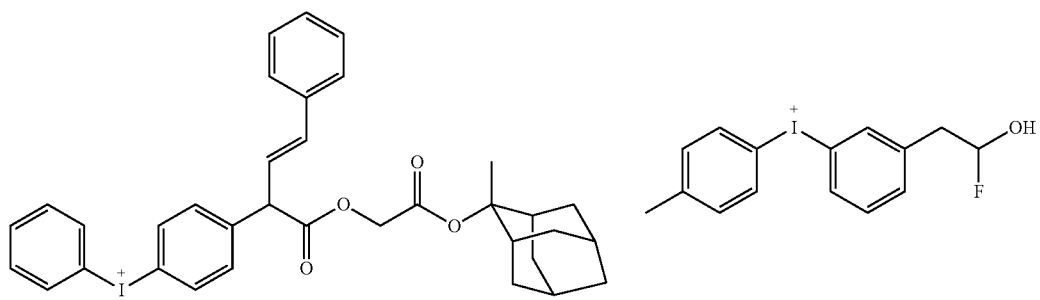
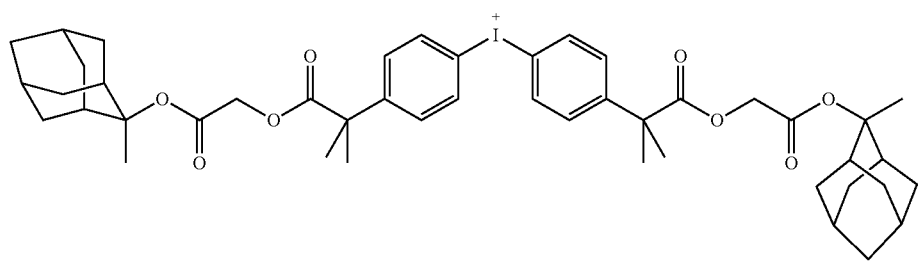
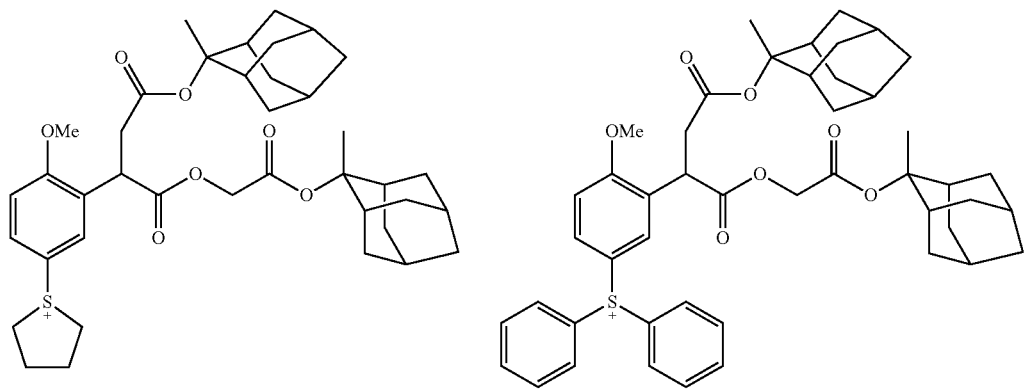
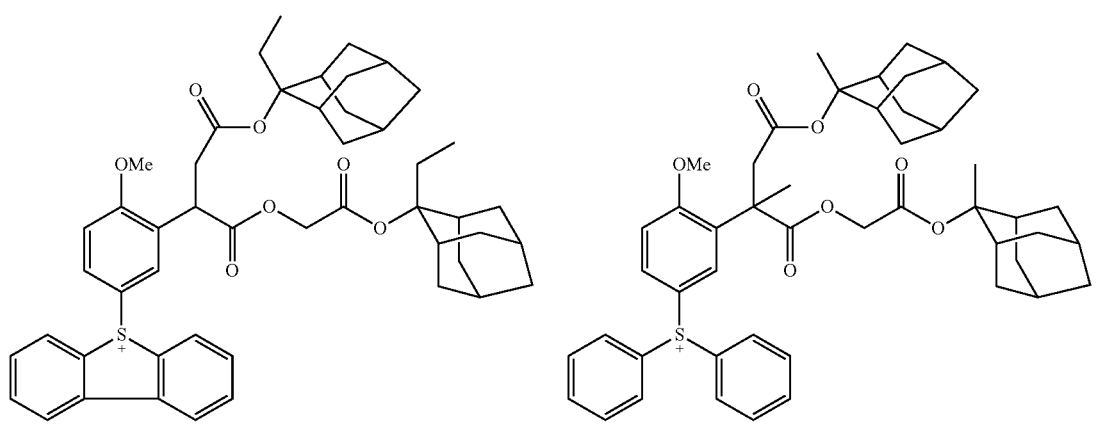

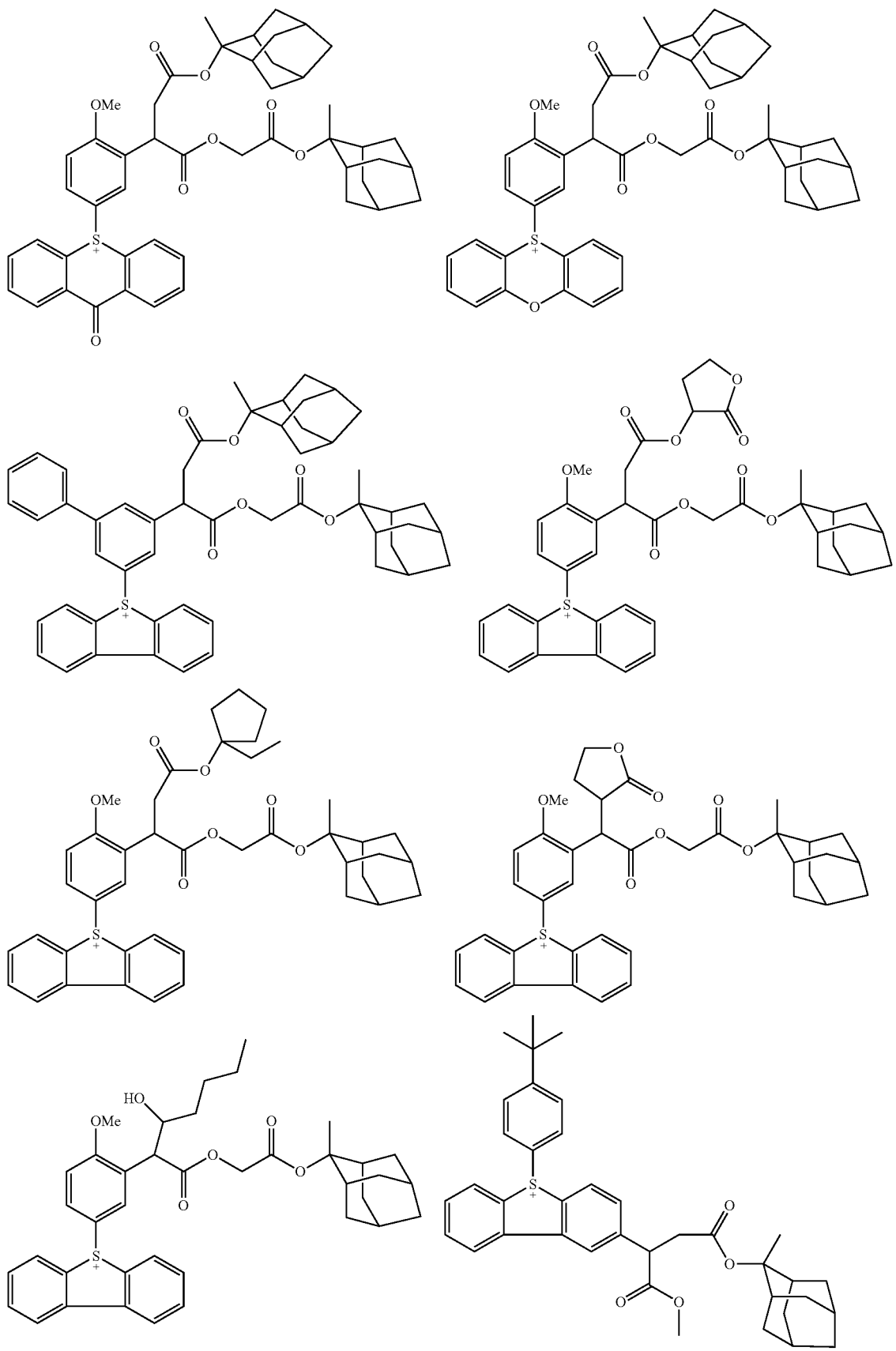

-continued
15
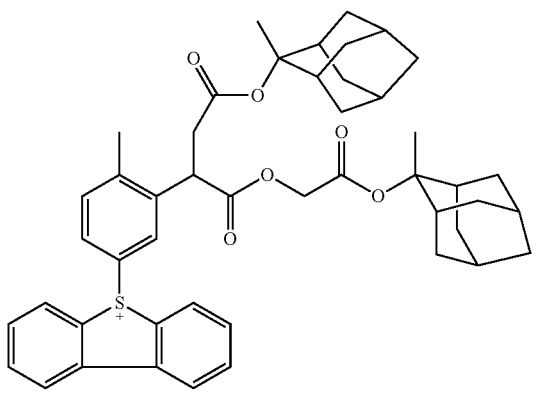
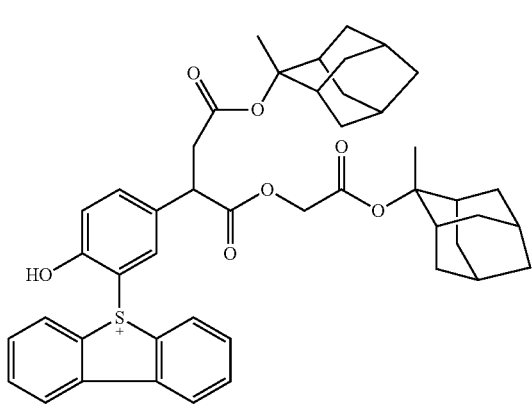
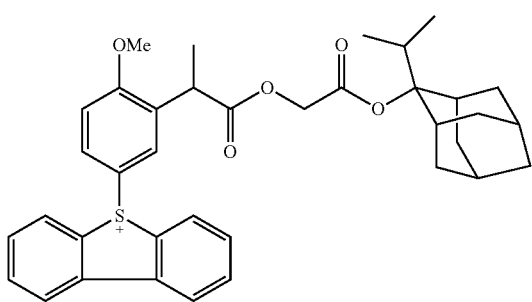
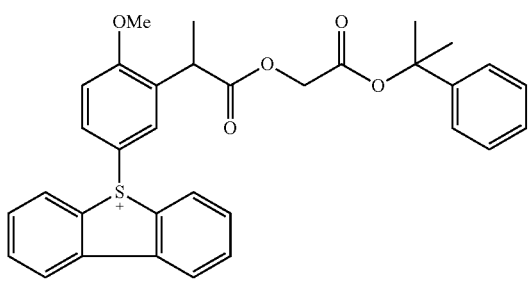
16
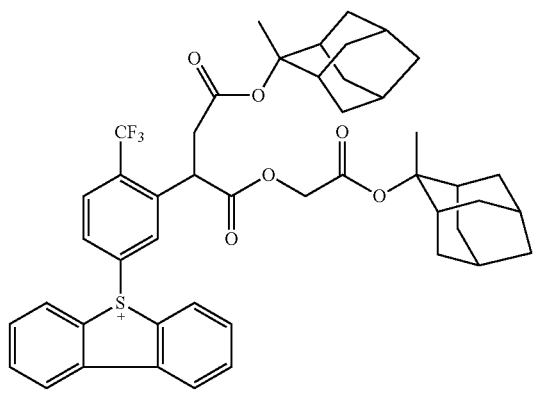
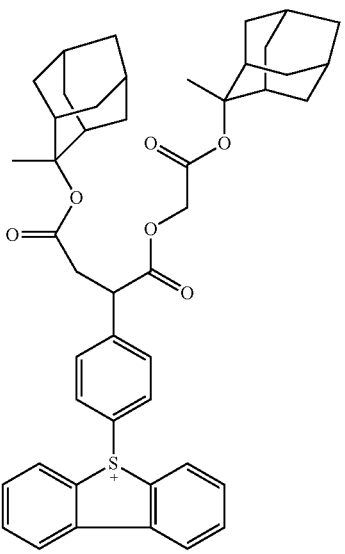
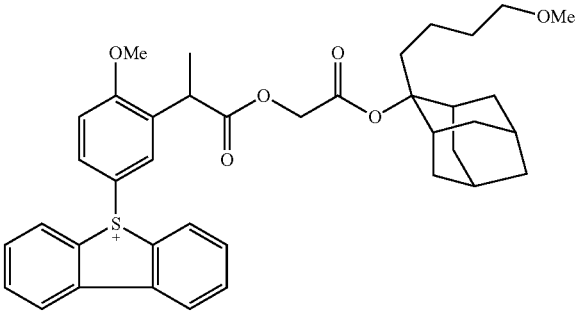
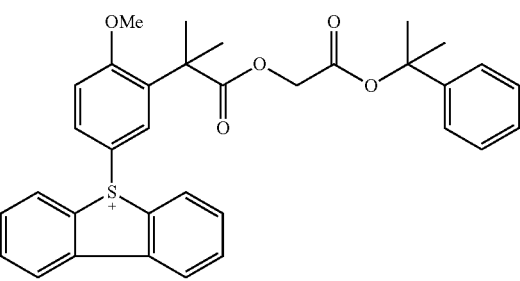

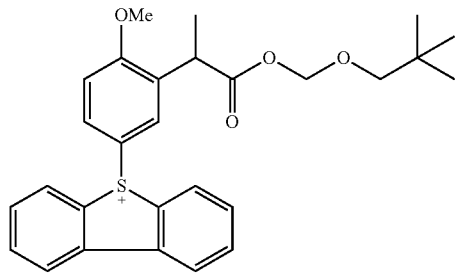
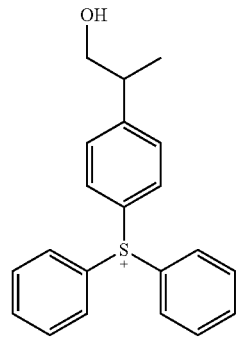
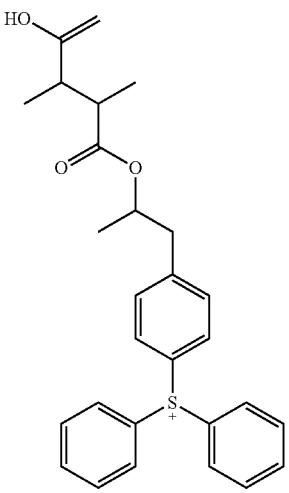
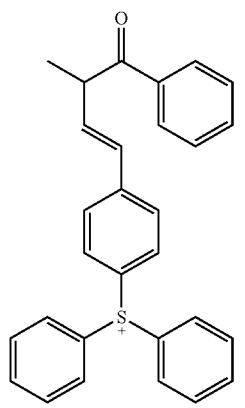
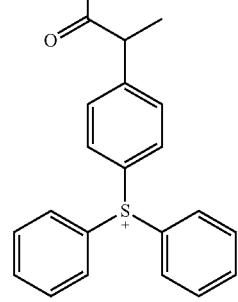
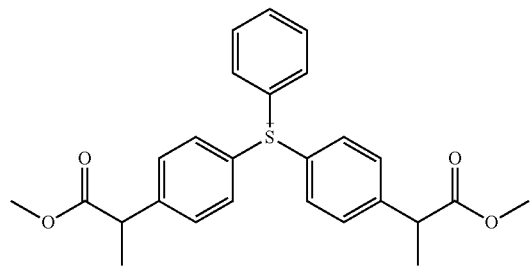
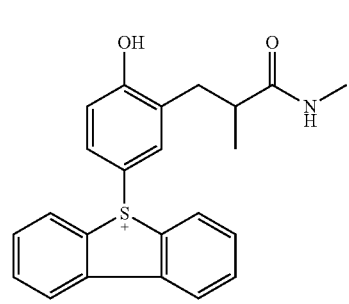
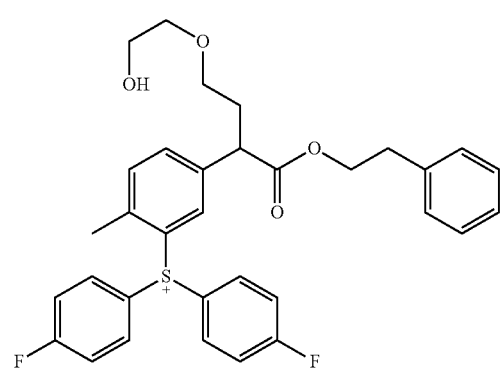

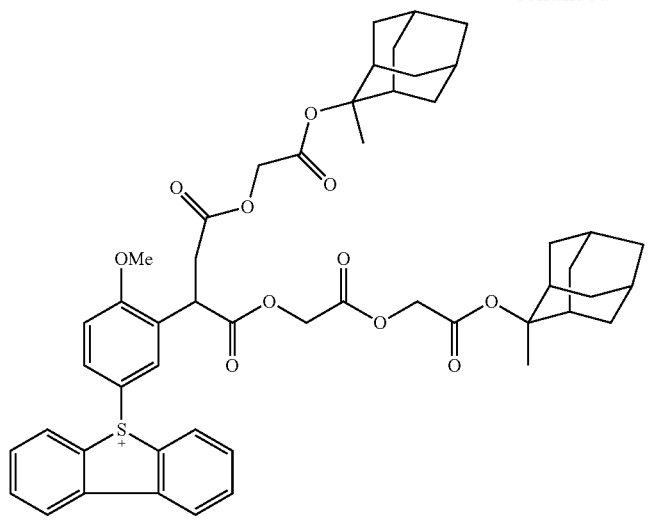
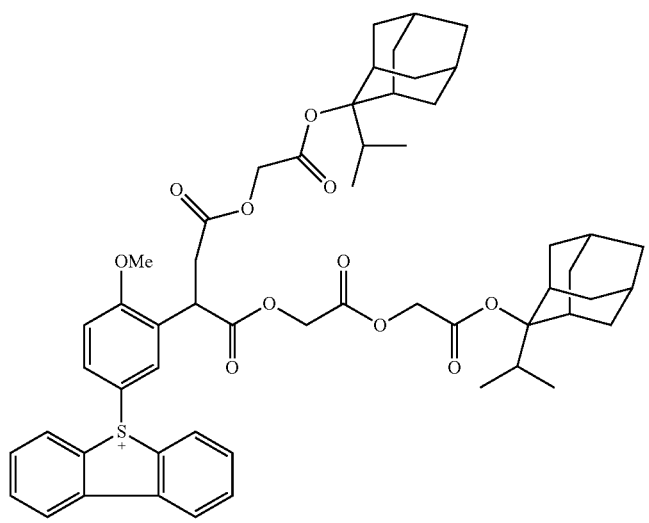
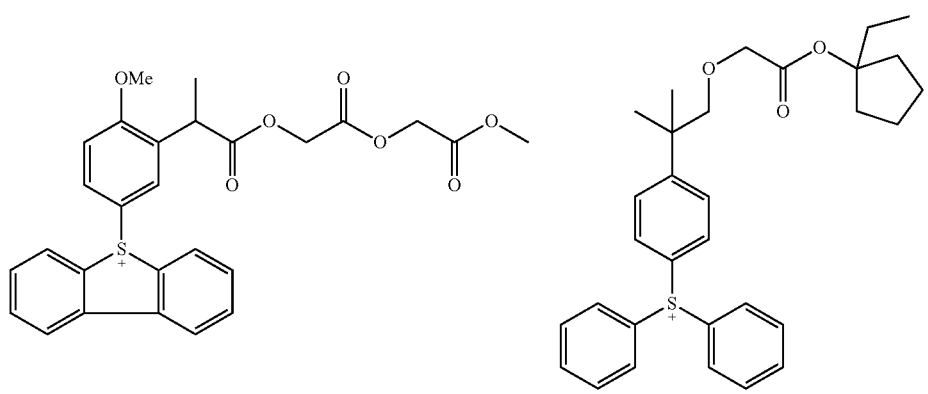

-continued
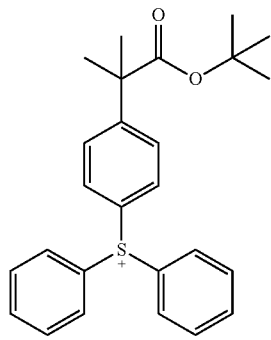
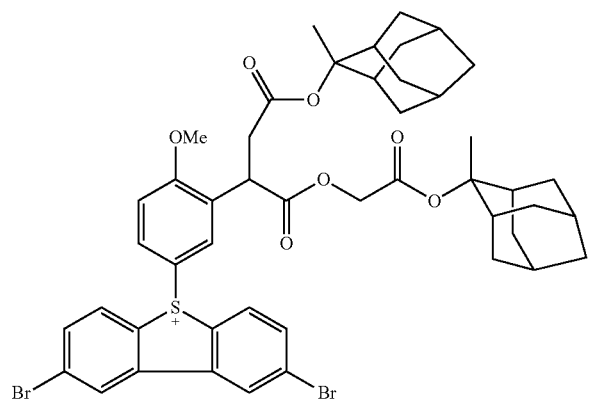
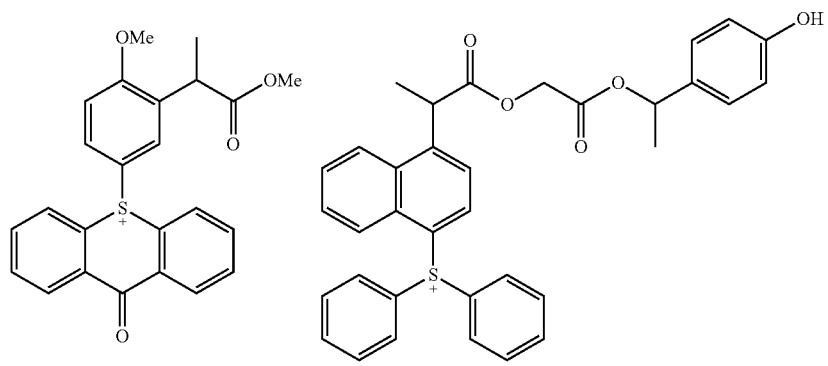
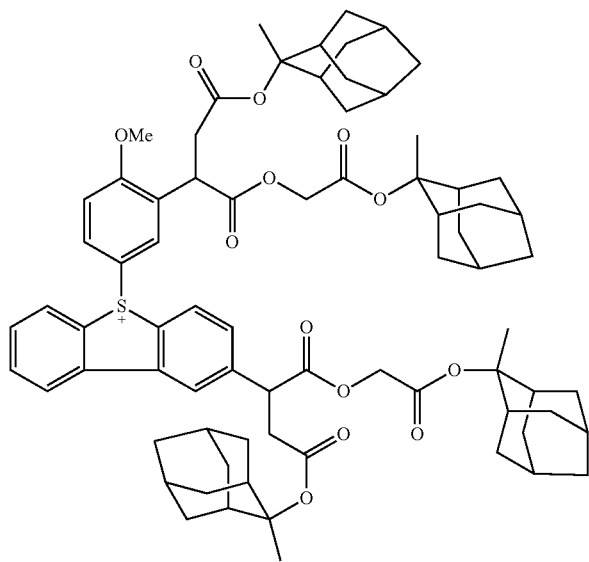

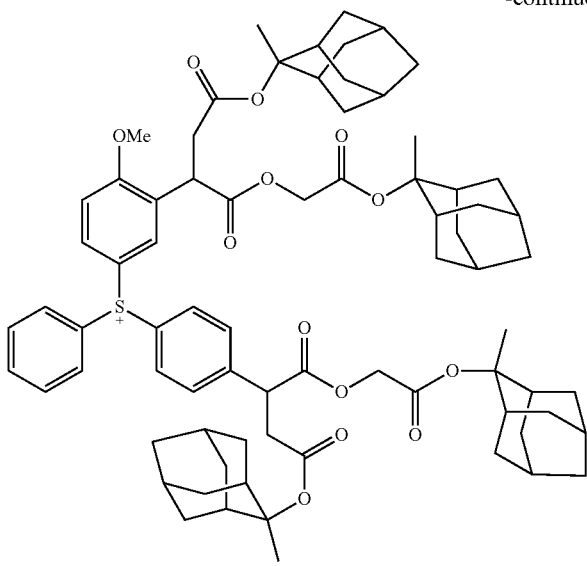

Preferred anion components (Z in the above formulae) of ionic acid generators of the invention include those where wherein the anion charge resides with a sulfonate group, a carboxylate group, a carbon atom, nitrogen atom or boron atom. Exemplary Z groups may comprises optionally substituted alkylsulfonate and optionally substituted carbocyclic arylsulfonate.

Preferred anion components (Z in the above formulae) of ionic acid generators of the invention include those of the following formula:

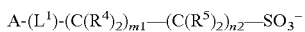

wherein A is a substituted or unsubstituted, monocyclic, polycyclic, or fused polycyclic $C_3$ or greater aliphatic or aromatic groups optionally comprising O, S, N, F, or a combination comprising at least one of the foregoing, or a $C_3$ or greater aliphatic or cycloaliphatic group containing a polymerizable double or triple bond. Preferred groups A include polycyclic aliphatic groups such as adamantyl groups, norbornenyl groups, and cycloalkylenyl groups substituted with hydroxy, ester, lactone, acetyl, ketyl, or combinations of these groups.

$R^4$ is H, a single bond, or a substituted or unsubstituted $C_{1-30}$ alkyl group, wherein when $R^4$ is a single bond, $R^4$ is covalently bonded to a carbon atom of A. Each $R^5$ is independently H, F, or $C_{1-4}$ fluoroalkyl, wherein at least one $R^5$ is not hydrogen. $L^1$ is a linking group comprising an —O—, —S—, —C(=O)—, carbonate, carboxylate, sulfonate, sulfate, or a sulfonamide group. Further, m1 is an integer of greater than or equal to 0, preferably 0 to 10, and also preferably 1 to 5, and n2 is an integer of greater than or equal to 0, preferably 1 to 10, and also preferably 1 to 5.

Exemplary anion components (Z in the above formulae) of ionic acid generators of the invention include the following:

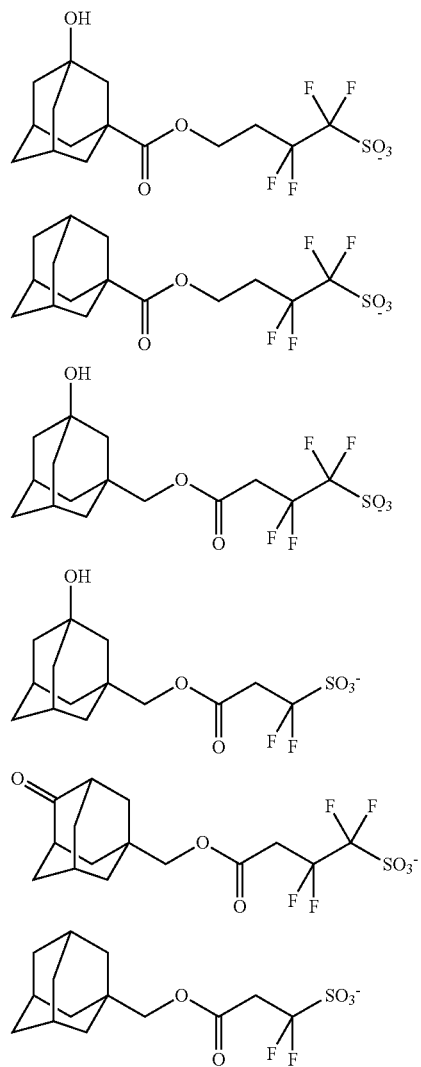

25
-continued
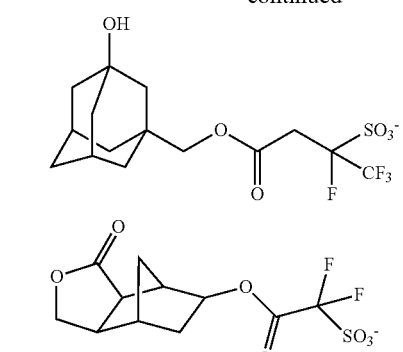
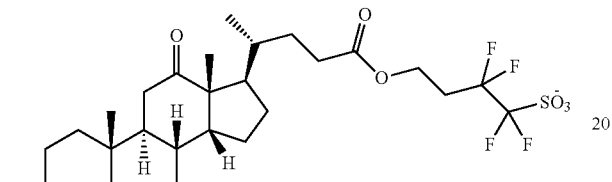
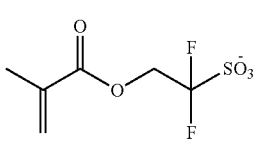
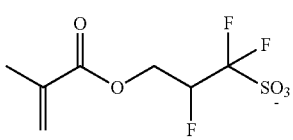
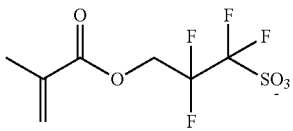
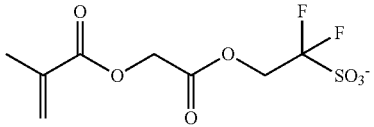
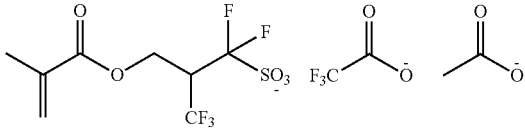
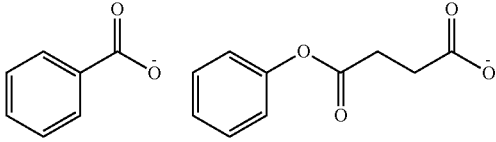
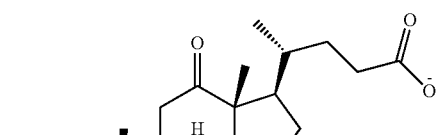
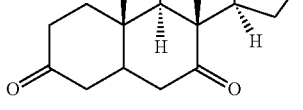
26
-continued
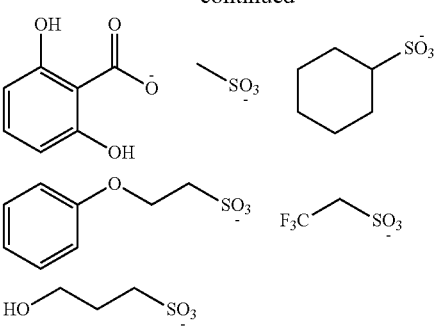
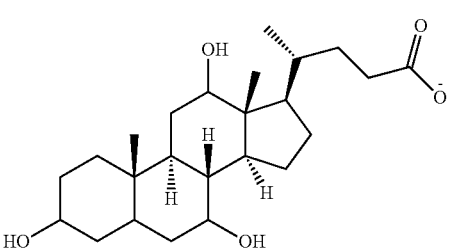
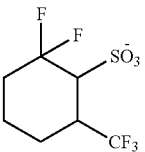
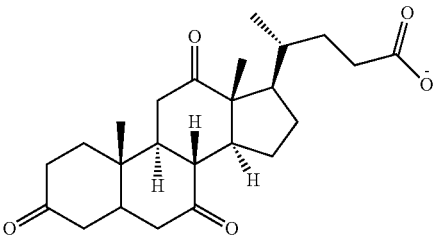
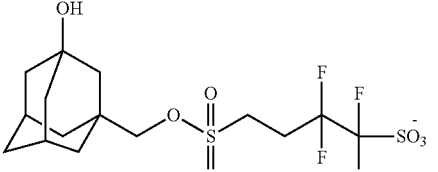
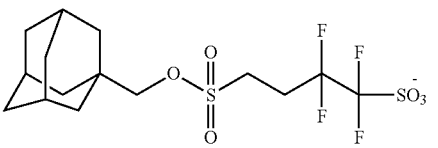
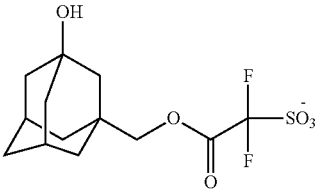
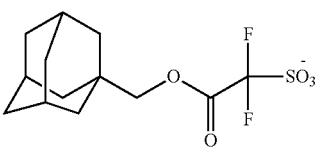

27
-continued
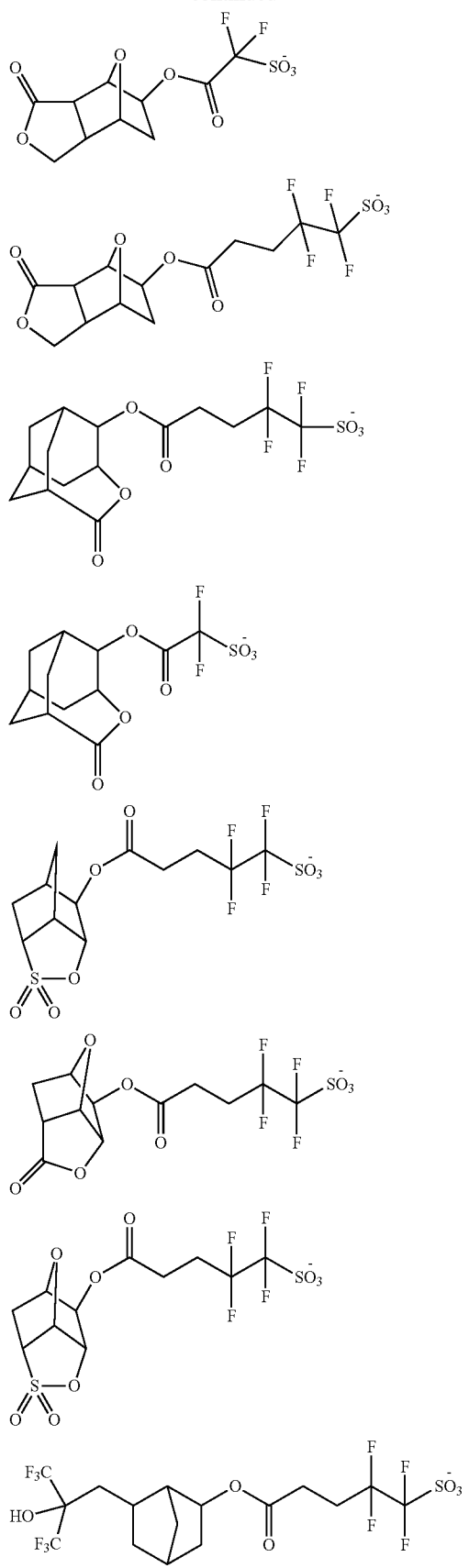
28
-continued
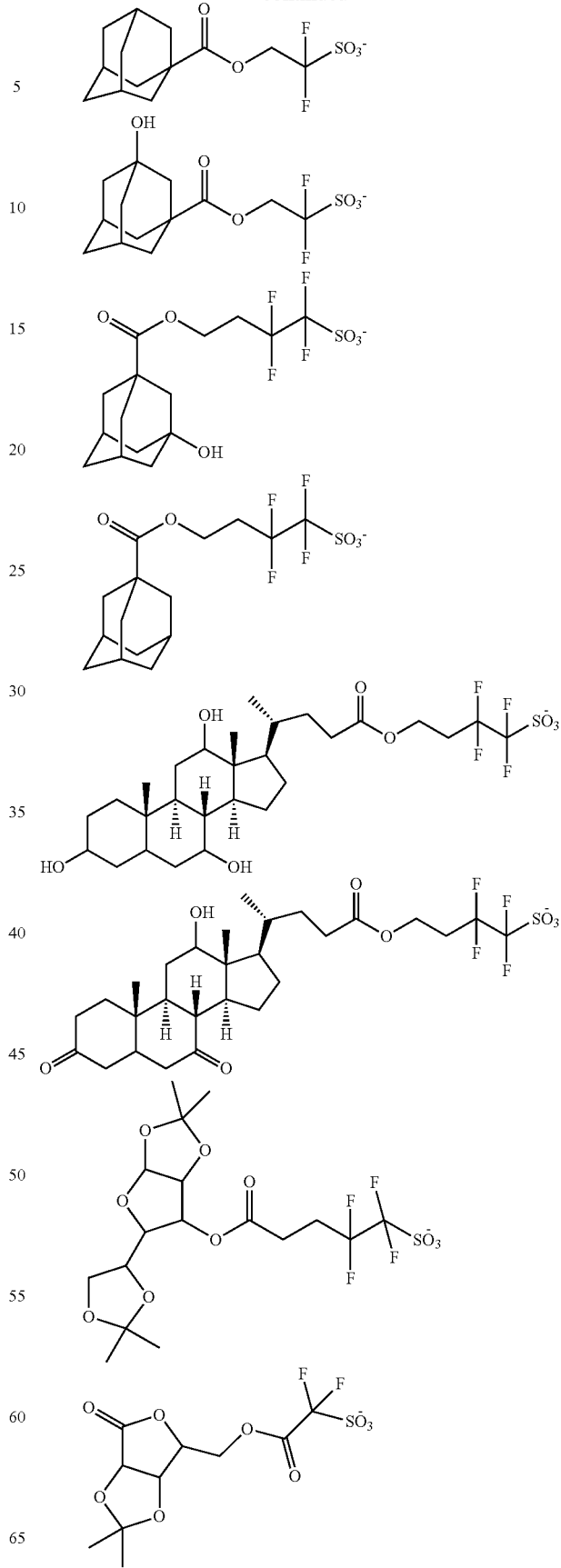

-continued
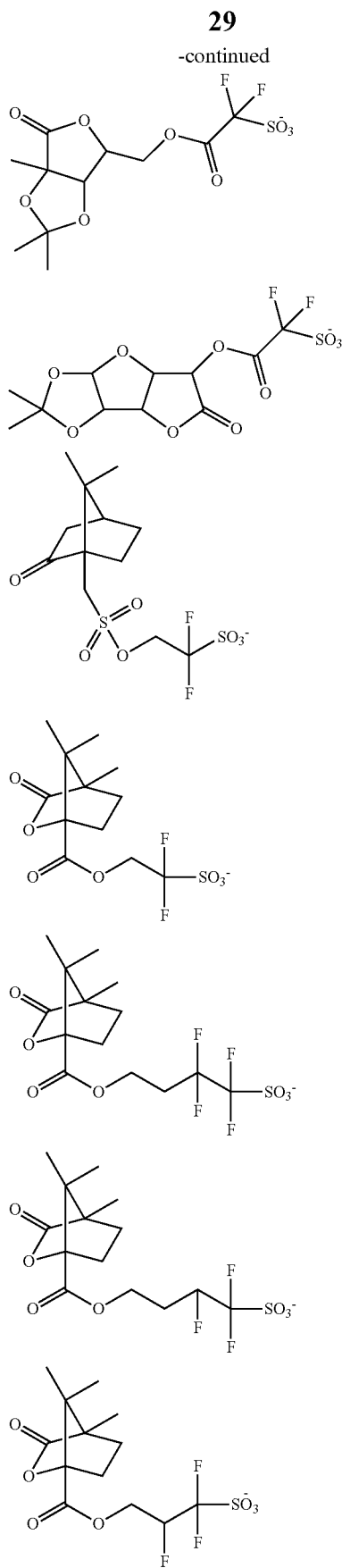
-continued
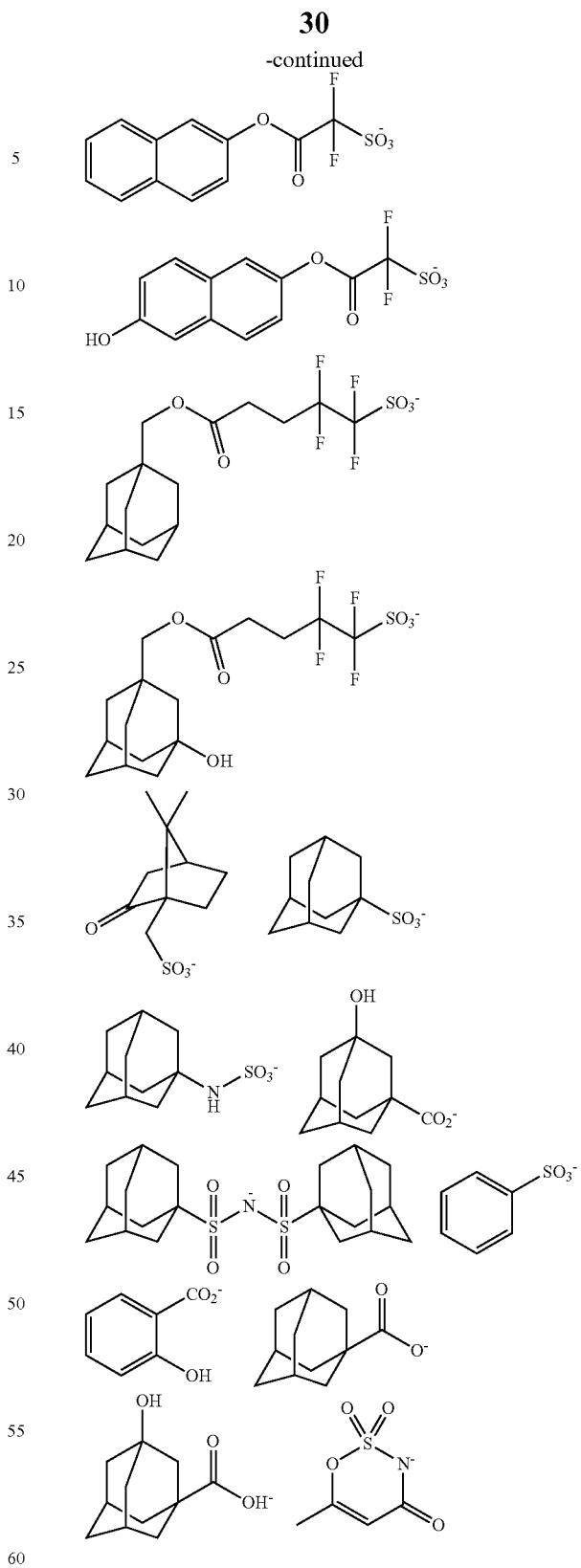
As mentioned above, acid generators of the invention may be covalently bound to a larger polymer. In certain embodiments, a resin or matrix polymer contains an ionic photoacid generator that comprises at least one diester moiety, wherein the ionic photoacid generator is bound to the resin or matrix polymer by the cation or anion.

For an ionic acid generator, suitably either cation or anion components are covalently linked to a larger polymer, or both cation and anion components are covalently bound to the polymer.

For instance, the anion component may comprise a polymerizable group (such as acrylate, methacrylate, vinyl ether) which can be reacted with a pre-formed polymer, or other monomers, to provide the polymer-bound acid generator. Exemplary polymerizable anion components include the following structures:

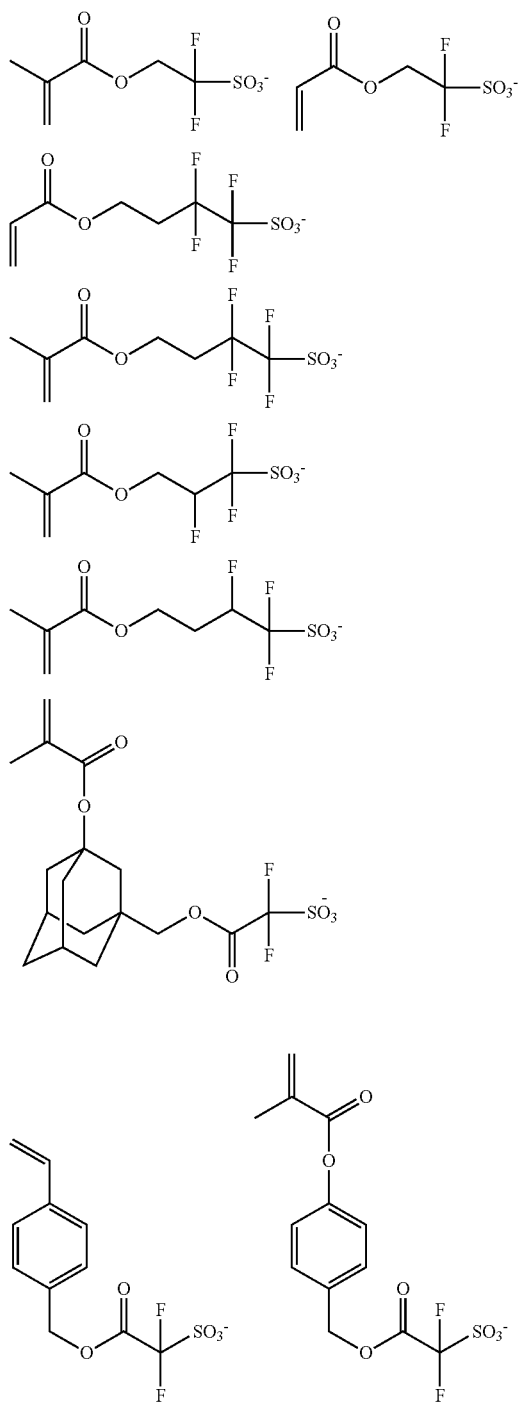

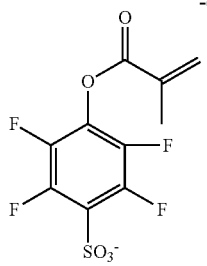

As discussed above, the present acid generator may be acid-labile and undergo a bond-breaking reaction during lithographic processing of a photoresist comprising the acid generator. As discussed above, an acid generator diester moiety itself may be photoacid-labile and react under lithographic processing of a photoresist comprising the acid generator. An acid generator also may comprise other substituents that are photoacid-labile. As referred to herein, acid-labile moieties or groups (including acid-labile esters and acetals) undergo reaction in the presence of generated acid (from an acid generator compound in a resist) during typical lithographic processing, including any post-radiation exposure thermal exposure. Acid-labile groups as referred to herein also may be referred to as photoacid-labile groups.

Suitable acid-labile groups of acid generators may be a variety of moieties, including acid-labile esters and acetals such as optionally substituted ethylcyclopentyl ester, methyladamantyl ester, ethyl adamantyl ester, t-butylester, phenyl ester, naphthyl ester and others. Suitable acid-labile groups of acid generators also may include groups of the following formula (IX) and ester photoacid-labile groups of the following formula X:

$$—O(CXY)_nR^3 \quad (IX)$$

wherein in Formula (IX), O is bound to any of R', R", A, Q, E, E', W, or R0 in Formula (I), more preferably as part of an ester moiety as part of E, E', or W, X and Y are independently hydrogen or a non-hydrogen substituent such as halogen (F, Cl, Br, I), $C_{1-10}$alkyl, $C_{1-10}$alkoxy; $R^3$ is a non-hydrogen substituent that provides an acid-labile moiety such as a carbamate, an acid-labile ester or acetal group; and n is a positive integer such as any of 1 through 20, more typically n is any of 1-10 or 1-4. Exemplary preferred $R^3$ groups include t-butyl, or more preferably a further ester linkage such as where $R^3$ is —$(CH_2)_n(C=O)O$-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl;

$$—(C=O)OR^3 \quad (X)$$

wherein in Formula (X), $R^3$ is a non-hydrogen substituent that provides an acid-labile moiety such as a carbamate, an acid-labile ester or acetal group. For instance, exemplary preferred $R^3$ groups include t-butyl, or more preferably a further ester linkage such as where $R^3$ is —$(CH_2)m(C=O)$O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl.

In certain aspects, an acid generator of the invention will not contain any acid-labile groups other than a diester moiety.

In the above formulae, suitable non-hydrogen substituents may be halo (F, Cl, Br or I); deuterium, cyano, nitro, hydroxy, optionally substituted $C_{1-20}$alkyl, optionally substituted $C_{1-20}$alkoxy, such as optionally substituted alkyl (e.g. optionally substituted $C_{1-10}$ alkyl), optionally substituted alkenyl or alkynyl preferably having 2 to about 20 carbon atoms such as such as allyl; optionally substituted ketones preferably having 1 to about 20 carbon atoms; optionally substituted alkylthio preferably having 1 to about 20 carbon atoms; optionally substituted alkylsulfinyl preferably 1 to about 20 carbon atoms; optionally substituted alkylsulfonyl preferably having 1 to about 20 carbon atoms; optionally substituted carboxy preferably have 1 to about 20 carbon atoms (which includes groups such as —COOR' where R' is H or $C_{1-8}$alkyl, including esters that are substantially non-reactive with photoacid); optionally substituted alkaryl such as optionally substituted benzyl, optionally substituted $C_{6-14}$ carbocyclic aryl such as optionally substituted phenyl, naphthyl, acenaphthyl, or optionally substituted heteroalicyclic or heteroaromatic group having from 5 to 14 atoms, including 1-4 heteroatoms selected from O, S, and N, in the ring system, such as pyridyl, furanyl, pyrrole, thiophene, furan, imidazole, pyrazole, oxazole, isoxazole, thiazole, isothiazole, triazole, furanzan, oxadiazole, thiadiazole, dithiazole, terazole, pyran, thiopyran, diazine, oxazine, thiazine, dioxine, dithine, and triazine and polyaromatic groups containing one or more of such moieties.

Preferred acid generators of the invention may comprise one or more electron withdrawing moieties, which suitably may be e.g. halogen such as Cl, Br or F with F being preferred, $C_{1-20}$haloalkyl with fluoroalkyl being preferred including perfluoroalkyl; cyano; nitro; $C_{1-20}$alkylsulfonyl, —COOH; and >C=O. For ionic acid generators, one or more electron withdrawing substituents may be on either cation or anion components.

As discussed, various moieties of acid generators and other materials may be optionally substituted. A "substituted" substituent may be substituted at one or more available positions, typically 1, 2, or 3 positions by one or more suitable groups such as e.g. halogen (particularly F, Cl or Br); cyano; nitro; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl, haloalkyl particularly $C_{1-8}$ haloalkyl such as $CF_3$; —CONHR, —CONRR' where R and R' are optionally substituted $C_{1-8}$alkyl; —COOH, COC, >C=O; and the like.

Acid generators of the invention can be readily prepared. Exemplary preferred syntheses are set forth in the examples which follow.

Photoresist Compositions

As discussed above, acid generators as disclosed herein are useful as the radiation sensitive component in photoresist compositions, including both positive-acting and negative-acting chemically amplified resist compositions. The acid generators of this invention may be used as part of: a cation or anion bound matrix resin or polymer; or a discrete blended acid generator in the presence of a matrix resin or polymer that may or may not contain an cation or anion bound acid generator.

The photoresists of the invention typically comprise a polymer and one or more acid generators as disclosed herein. Preferably the polymer has functional groups that impart alkaline aqueous developability to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generators are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-deprotectable monomer having the following formula (XI), a lactone- or sultone-containing monomer of the following formula (XII), a base-soluble monomer of the following formula (XIII) for adjusting dissolution rate in alkaline developer, and a photoacid-generating monomer of the following formula (XIV), or a combination comprising at least one of the foregoing monomers:

wherein each $R^a$ is independently H, F, —CN, $C_{1-10}$ alkyl, or $C_{1-10}$ fluoroalkyl. In the acid-deprotectable monomer of formula (XI), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In the lactone- or sultone-containing monomer of formula (XII), L is a monocyclic, polycyclic, or fused polycyclic $C_{4-20}$ lactone- or sultone-containing group. In the base solubilizing monomer of formula (XIII), W is a halogenated or non-halogenated, aromatic or non-aromatic $C_{2-50}$ hydroxyl-containing organic group having a pKa of less than or equal to 12. In the photoacid generating monomer of formula (XIV), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, Z is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

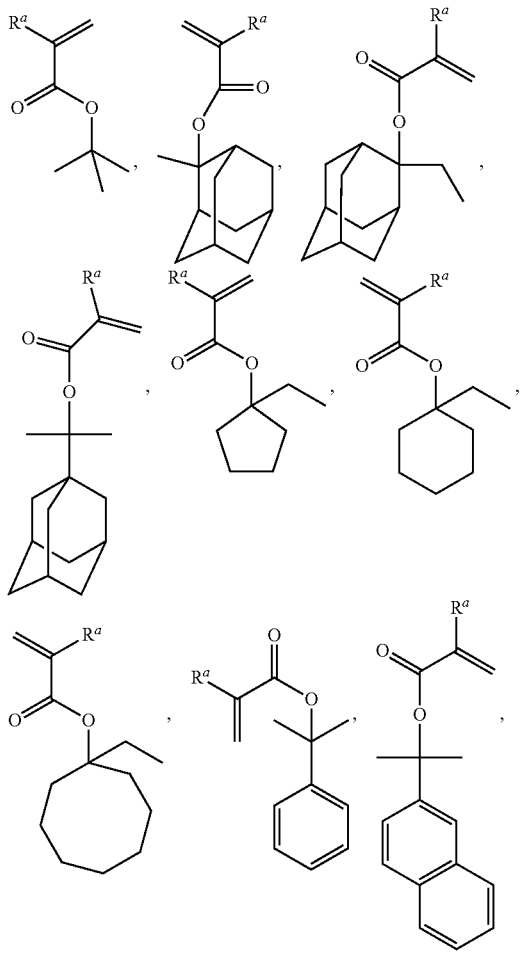

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (XV):

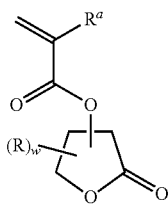

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (XV), R is attached directly to the lactone ring or commonly attached to the lactone ring and/or one or more R groups, and the ester moiety is attached to the lactone ring directly, or indirectly through R.

Exemplary lactone-containing monomers include:

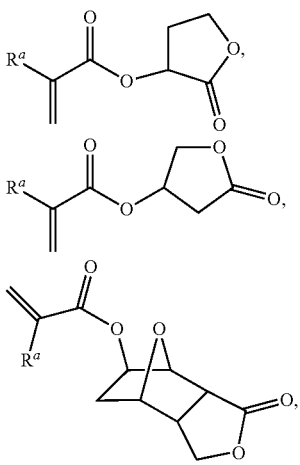

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (XVI):

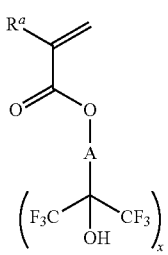

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

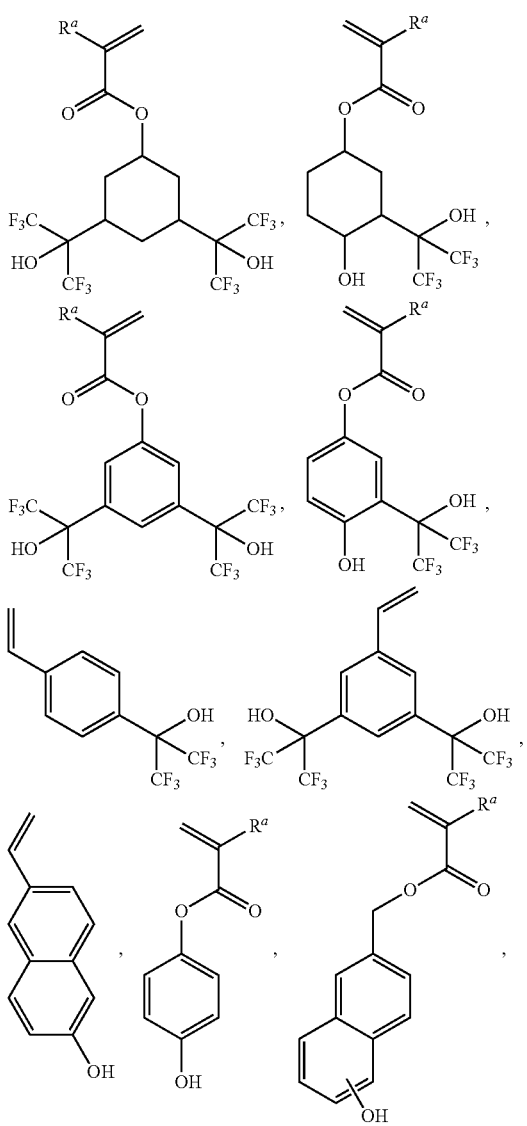

or a combination comprising at least one of the foregoing, wherein $R^a$ is H, F, —CN, $C_{1-6}$ alkyl, or $C_{1-6}$ fluoroalkyl.

Preferred photoacid generating monomer include those of the formulae (XVII) or (XVIII):

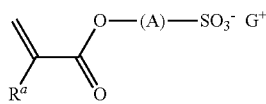

(XVII)

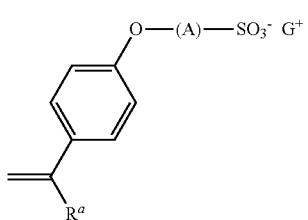

(XVIII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XVII) and (XVIII), A is a —[(C($R^1$)$_2$)$_x$C(=O)O]$_b$—C(($R^2$)$_2$)$_y$(CF$_2$)$_z$— group, or an o-, m- or p-substituted —C$_6$F$_4$— group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred photoacid generating monomers include:

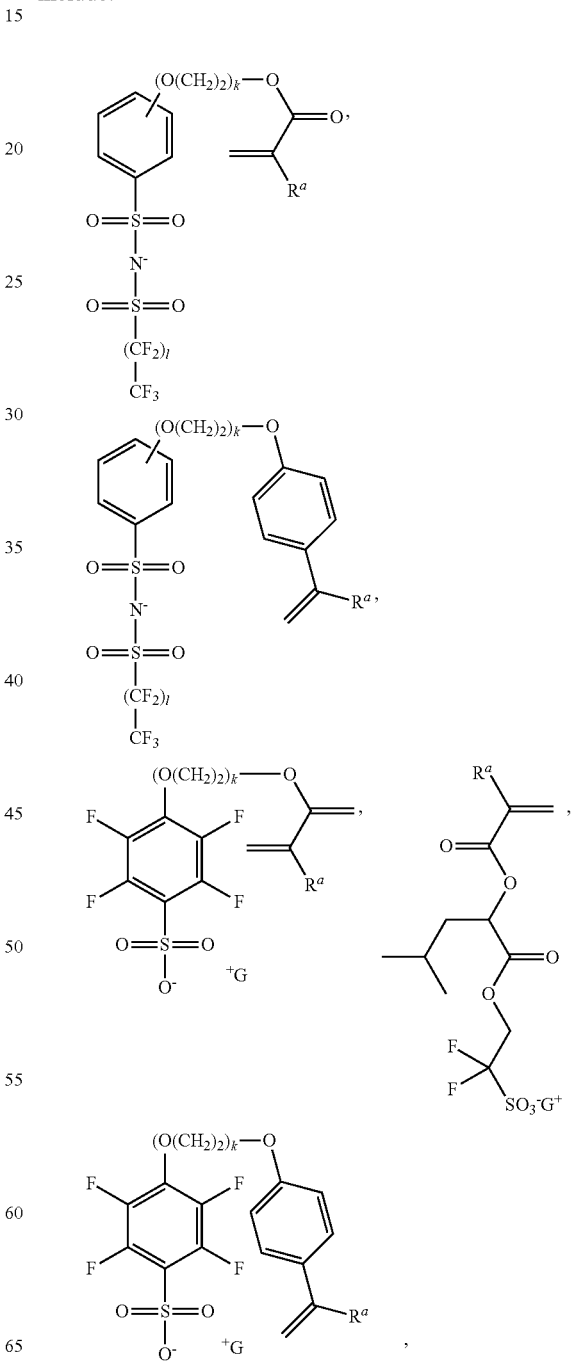

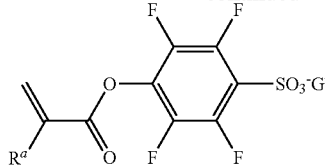
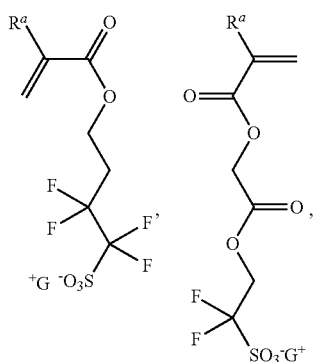

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation.

Preferred photoacid-generating monomers may include sulfonium or iodonium cation. Preferably, in the formulae above, $G^+$ is of the formula (XIX):

(XIX)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a covalent bond, such as a single bond, and a is 2 or 3, wherein when X is I, a is 2, or when X is S, a is 3.

Exemplary acid generating monomers include those having the formulas:

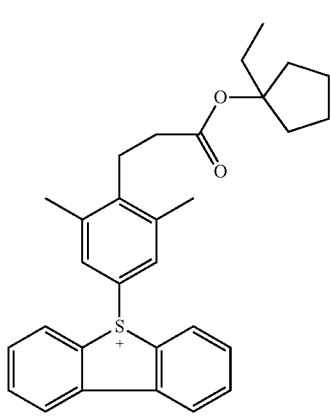

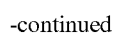
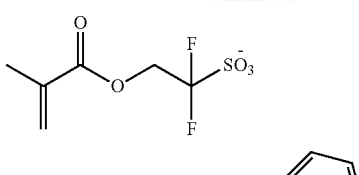
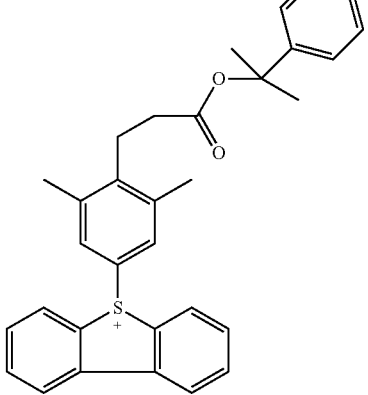
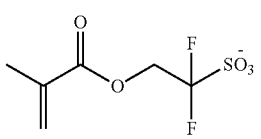
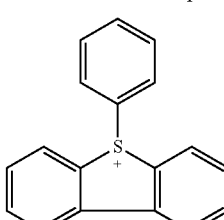
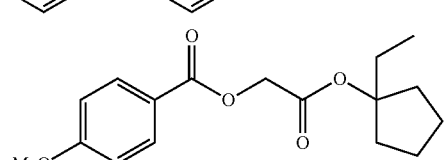
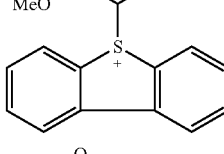
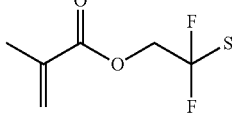
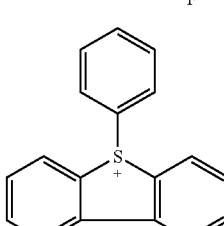
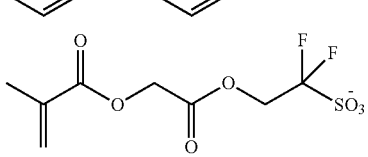

41
-continued

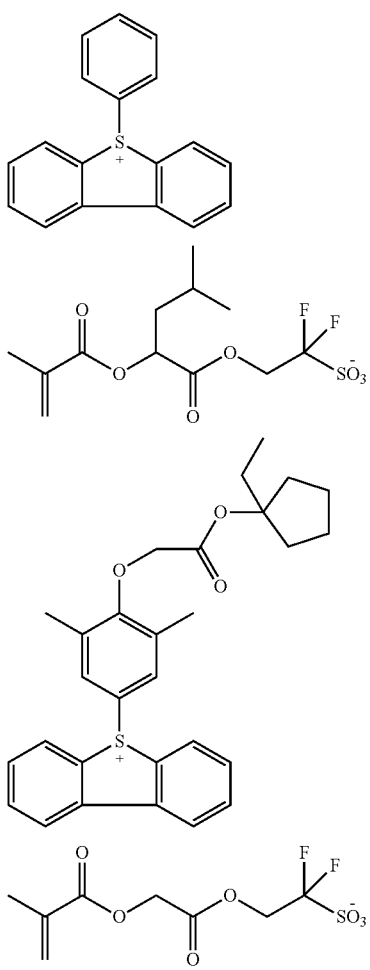

42
-continued

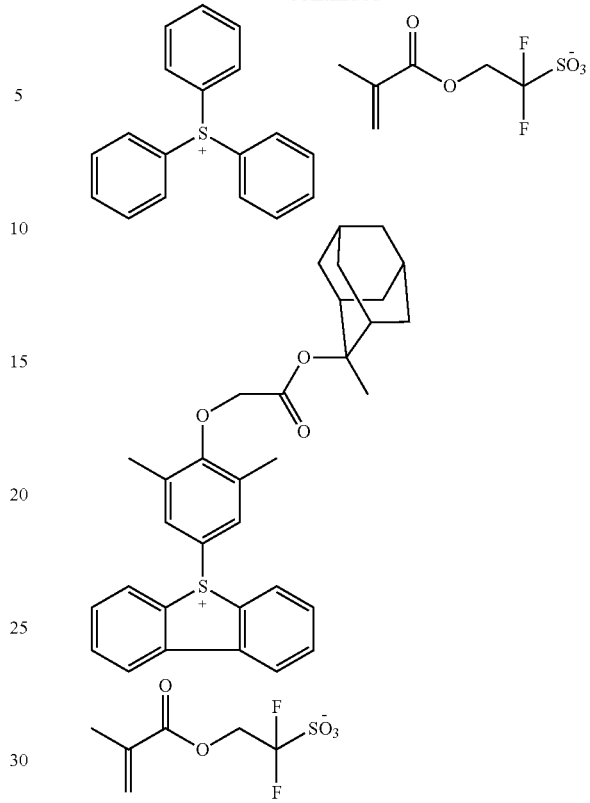

Specifically suitable polymers that have acid-labile deblocking groups for use in a positive-acting chemically-amplified photoresist of the invention have been disclosed in US Patent Application 20130209934, European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydisperity. Suitable polymers include those that have an $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and one, two, or more photoacid generators as disclosed herein. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Photoresists of the invention also may contain other materials. For example, other optional additives include actinic and contrast dyes, anti-striation agents, plasticizers, speed enhancers and sensitizers. Such optional additives typically will be present in minor concentration in a photoresist composition.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, tris(2-hydroxypropyl)amine, oltetrakis (2-hydroxypropyl)ethylenediamine; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the polymer in an amount of 50 to 99 wt %, specifically 55 to 95 wt %, more specifically 60 to 90 wt %, and still more specifically 65 to 90 based on the total weight of solids. A photo-destroyable base may be present in the photoresist in an amount of 0.01 to 5 wt %, specifically 0.1 to 4 wt %, and still more specifically 0.2 to 3 wt %, based on the total weight of solids. Photo-destroyable bases include photo-decomposable cations, and preferably those also useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 50 wt %, specifically less than or equal to 35%, or more specifically less than or equal to 25%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent.

The acid generator(s) should be present in an amount sufficient to enable generation of a latent image in a coating layer of the resist. More specifically, the photoacid generator(s) will suitably be present in an amount of from about 1 to 50 weight percent of total solids of a resist. It will be understood that the solids includes polymer, quencher, surfactant, and any optional additives, exclusive of solvent.

A coated substrate may be formed from the photoresist containing acid generators which should be present in an amount sufficient to enable generation of a latent image in a coating layer of the resist and acid generators. Such a coated substrate includes: (a) a substrate having one or more layers to be patterned on a surface thereof; and (b) a layer of the photoresist composition including the acid generator over the one or more layers to be patterned. For EUV or e-beam imaging, photoresists may suitably have relatively higher content of acid generator compounds, e.g. where the one or more acid generators comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and tetrahydrofuran.

The photoresist may, when used in one or more such a pattern-forming processes, be used to fabricate electronic and optoelectronic devices such as memory devices, processor chips (CPU's), graphics chips, and other such devices.

EXAMPLE 1

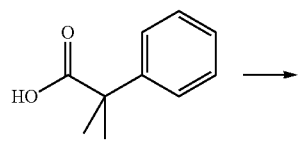

Bis(4-(2-carboxypropan-2-yl)phenyl)iodonium bromide 2-methyl-2-phenylpropanoic acid (10 g, 60.9 mmol) was suspended in a 1:1 mixture of sulfuric acid and acetic acid (90 mL) and heated to 55° C. where $NaIO_4$ (23.4 mmol, 5.00 g) was slowly added in portions over 90 minutes followed by additional heating for 1 h. The reaction mixture was cooled, poured onto ice water (1 L) and extracted with methyl t-butyl ether (MTBE) (3×350 mL). KBr (0.609 mol, 72.4 g) in water (100 mL) was added to the aqueous layer and extracted with dichloromethane (DCM) (3×300 mL). The combined organic layers concentrated and the crude residue recrystallized from heptanes, ethyl acetate and acetone to afford the title compound (5.27 g, 42%) as a white solid. $^1$H NMR (300 MHz, $(CD_3)_2SO$) δ: 12.6 (brs, 2COOH), 8.16 (d, J=8.1 Hz, 4H), 7.45 (d, J=8.1 Hz, 4H), 1.43 (2, 12H).

EXAMPLE 2

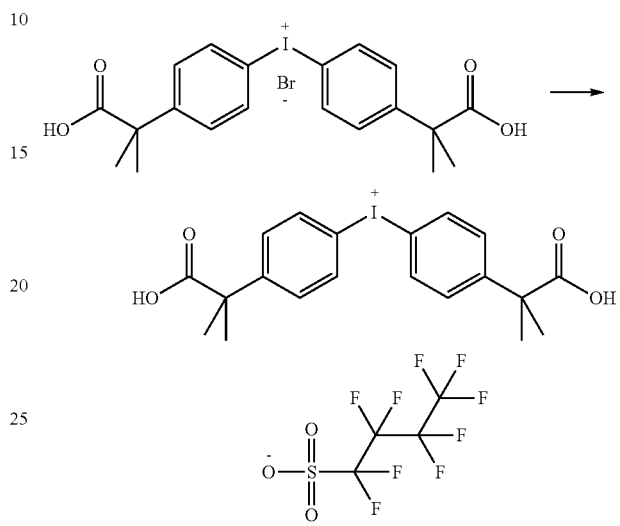

Bis(4-(2-carboxypropan-2-yl)phenyl)iodonium 1,1,2,2,3,3,4,4,4-nonafluorobutane-1-sulfonate Bis(4-(2-carboxypropan-2-yl)phenyl)iodonium bromide (1.53 g, 2.87 mmol) and potassium 1,1,2,2,3,3,4,4,4-nonafluorobutane-1-sulfonate (3.16 mmol, 1.07 g) were dissolved in DCM (50 mL) and water (50 mL) and stirred overnight. The layers were separated, the aqueous phase extracted with DCM (2×100 mL), the combined organics washed with water (2×100 mL) and concentrated to afford the title compound (1.25 g, 58%) as a white solid.

$^1$H NMR (300 MHz, $(CD_3)_2CO$) δ: 11.4 (brs, 2COOH), 8.34 (d, J=7.8 Hz, 4H), 7.64 (d, J=7.8 Hz, 4H), 1.57 (s, 12H).

EXAMPLE 3

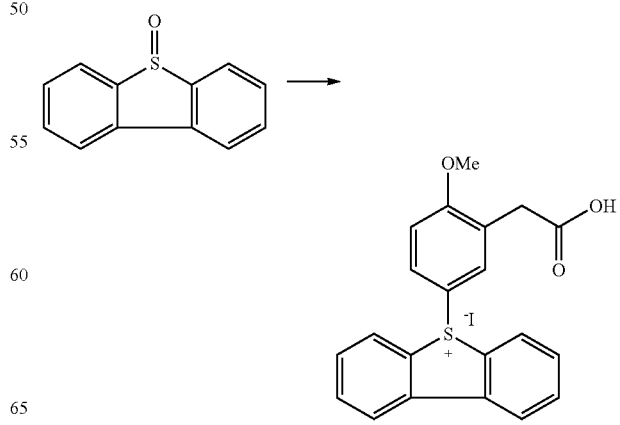

5-(3-(Carboxymethyl)-4-methoxyphenyl)-dibenzothiophenium iodide

Eaton's Reagent (phosphorus pentoxide solution in methanesulfonic acid) (400 mL) was added to a solution of 2-methoxyphenylacetic acid (140 g, 0.843 mol) and dibenzothiophene oxide (160 g, 0.800 mol) in dichloromethane (400 mL), stirred at 25° C. for 18 h, cooled to 0° C. and carefully quenched with water (1 L). The aqueous mixture was washed with MTBE (3×500 mL) and the aqueous phase poured onto aqueous sodium iodide (300 g in 3 L) followed by vigorously stirred for 1 h. The precipitate was filtered, washed with water (3×1 L), acetone (1 L) and MTBE (2×500 mL) to afford the title compound as a white solid (360 g, 94%). $^1$H NMR (500 MHz, (CD$_3$)$_2$SO) δ: 12.30 (brs, COOH), 8.52 (d, J=7.5 Hz, 2H), 8.31 (d, J=8.5 Hz, 2H), 7.95 (t, J=7 Hz, 2H), 7.75 (t, J=8 Hz, 2h), 7.70 (dd, J=9, 2 Hz, 1H), 7.31 (d, J=2 Hz, 1H), 7.23 (d, J=8.5 Hz, 1H), 3.82 (s, 3H), 3.46 (s, 2H).

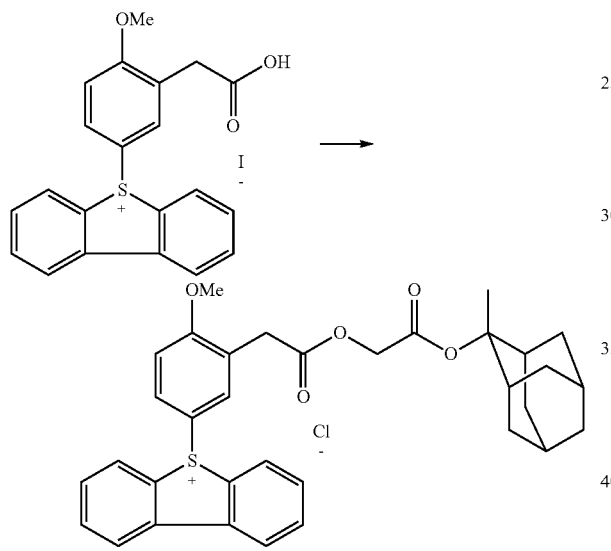

EXAMPLE 4

5-(4-methoxy-3-(2-(2-((2-methyladamantan-2-yl)oxy)-2-oxoethoxy)-2-oxoethyl)phenyl)-dibenzothiophenium chloride 5-(3-(carboxymethyl)-4-methoxyphenyl)-dibenzothiophenium iodide (15.0 g, 31.5 mmol) was dissolved in DMF (100 mL) and degassed with nitrogen for 30 min, then 2-methyladamantan-2-yl 2-chloroacetate (7.49 g, 31.0 mmol) and cesium carbonate (14.4 g, 44.1 mmol) were added sequentially and the mixture stirred at 25° C. for 6 h. The solution was diluted with water (200 mL), extracted with DCM (2×150 mL), the combined organic layers washed with water (5×150 mL) and concentrated to a viscous oil which was poured onto MTBE (1 L) and vigorously stirred for 1 h. The precipitate was filtered, washed with MTBE (2×250 mL) and dried to afford the title compound (18.2 g, 99%) as a white solid. $^1$H NMR (300 MHz, (CD$_3$)$_2$SO) δ: 8.51 (d, J=8.1 Hz, 2H), 8.29 (d, J=8.1 Hz, 2H), 7.95 (t, J=7.5 Hz, 2H), 7.70-7.81 (m, 3H), 7.32 (d, J=2.1 Hz, 1H), 7.25 (dd, J=7.5, 2.1 Hz, 1H), 4.56 (s, 2H), 3.82 (s, 3H), 3.65 (s, 2H), 2.10-2.19 (m, 2H), 1.61-1.95 (m, 11H), 1.52 (s, 3H), 1.39-1.50 (m, 2H).

EXAMPLE 5

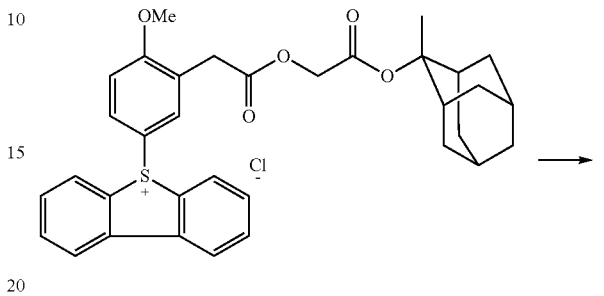

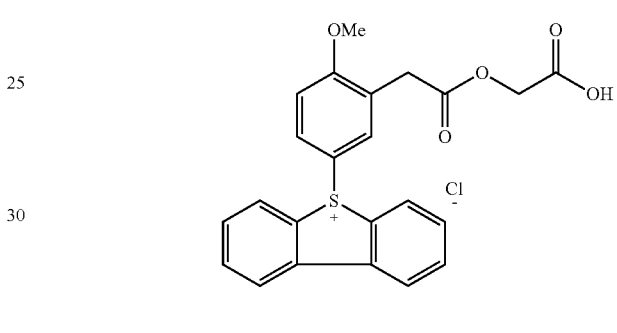

5-(3-(2-(carboxymethoxy)-2-oxoethyl)-4-methoxyphenyl)-dibenzothiophenium chloride Triflic acid (trifluoromethanesulfonic acid) (0.5 mL) was added to a solution of 5-(4-methoxy-3-(2-(2-((2-methyladamantan-2-yl)oxy)-2-oxoethoxy)-2-oxoethyl)phenyl)-dibenzothiophenium chloride (3.00 g, 5.07 mmol) in DCM (50 mL) and stirred at 25° C. for 48 h. The precipitate was filtered, washed with MTBE:Acetone (50 mL) and MTBE (2×100 mL) to afford the title compound (2.05 g, 91%) as a white solid. $^1$H NMR (300 MHz, (CD$_3$)$_2$SO) δ: 12.5 (brs, COOH), 8.52 (d, J=7.8 Hz, 2H), 8.29 (d, J=8.1 Hz, 2H), 7.95 (t, J=7.5 Hz, 2H), 7.67-7.79 (m, 3H), 7.38 (vis s, 1H), 7.22 (d, J=8.1 Hz, 1H), 4.51 (s, 2H), 3.81 (s, 3H), 3.66 (s, 2H).

EXAMPLE 6

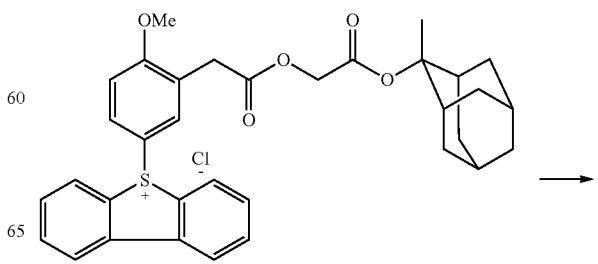

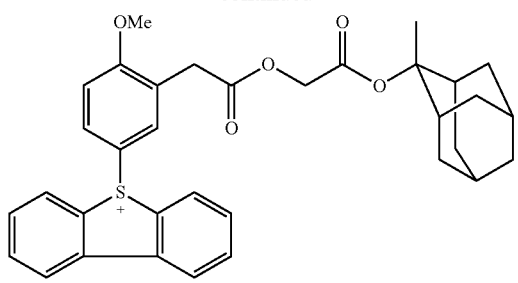

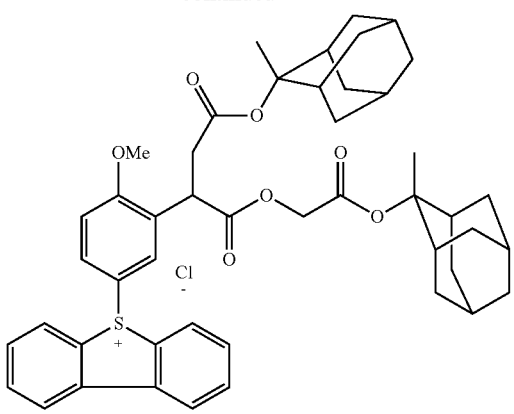

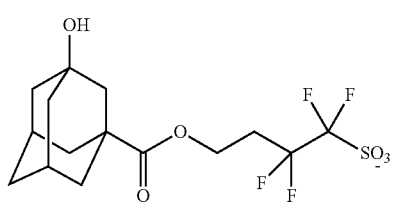

5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride 5-(4-methoxy-3-(2-(2-((2-methyladamantan-2-yl)oxy)-2-oxoethoxy)-2-oxoethyl)phenyl)-dibenzothiophenium 1,1,2,2-tetrafluoro-4-((3-hydroxyadamantane-1-carbonyloxy)butane-1-sulfonate 5-(4-methoxy-3-(2-(2-((2-methyladamantan-2-yl)oxy)-2-oxoethoxy)-2-oxoethyl)phenyl)-dibenzothiophenium chloride (6.75 g, 11.4 mmol) and sodium 3-hydroxyadamantane-acetoxy-1,1,2,2-tetrafluorobutane-1-sulfonate (11.4 mmol, 4.87 g) were dissolved in DCM (150 mL) and water (150 mL) and stirred at 25° C. overnight. The layers were separated, the aqueous phase extracted with dichloromethane (70 mL), the combined organic layers washed with water (10×150 mL) and concentrated under reduced pressure to afford the title compound (8.86 g, 81%) as a white solid. $^1$H NMR (500 MHz, (CD$_3$)$_2$CO) δ: 8.53 (d, J=8 Hz, 2H), 8.36 (d, J=8 Hz, 2H), 8.02 (t, J=7.5 Hz, 2H), 7.85 (dd, J=9, 2 Hz, 1H), 7.82 (t, J=7.5 Hz, 2H), 7.63 (d, J=2 Hz, 1H), 7.31 (d, J=9 Hz, 1H), 4.58 (s, 2H), 4.34 (t, J=6.5 Hz, 2H), 3.96 (s, 3H), 3.70 (s, 2H), 3.58 (s, 10H), 2.71 (tt, J=18.5, 7 Hz, 2H), 2.14-2.28 (m, 4H), 1.87-2.40 (m, 5H), 1.50-1.83 (m, 23H).

5-(3-(carboxymethyl)-4-methoxyphenyl)-dibenzothiophenium iodide (100 g, 210 mmol) was dissolved in DMF (400 mL), degassed with nitrogen for 30 min, and cooled to 0° C. followed by the sequential addition of 2-methyladamantan-2-yl 2-chloroacetate (122 g, 504 mmol), sodium iodide (63 g, 420 mmol) and cesium carbonate (171 g, 525 mmol). The mixture was slowly warmed to room temperature, stirred for 48 h and poured onto ice water (1 L). The solution was extracted with DCM (3×300 mL), the combined organics concentrated and recrystallized from methanol followed by purification via silica gel flash column chromatography (neutralized TEA, eluting DCM) to afford the title compound (111 g, 66%) as a white solid. $^1$H NMR (500 MHz, (CD$_3$)$_2$CO) δ: 8.52-8.56 (m, 2H), 8.46 (d, J=8 Hz, 1H), 8.39 (d, J=8 Hz, 1H), 8.0-8.07 (m, 2H), 7.85 (d, J=2.5 Hz, 1H), 7.77-7.84 (m, 2H), 7.67 (dd, J=8.5, 2 Hz, 1H), 7.29 (d, J=9 Hz, 1H), 5.62 (s, 2H), 4.55-4.65 (m, 2H), 4.40-4.45 (m, 1H), 3.98 (s, 3H), 3.0-3.07 (m, 2H), 2-65-2.71 (m, 2H), 1.44-2.30 (m, 27H).

EXAMPLE 7

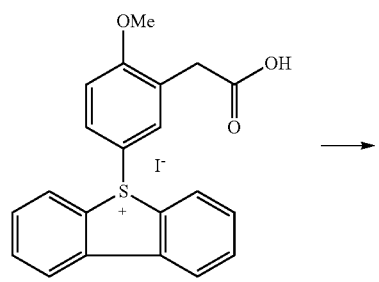

EXAMPLE 8

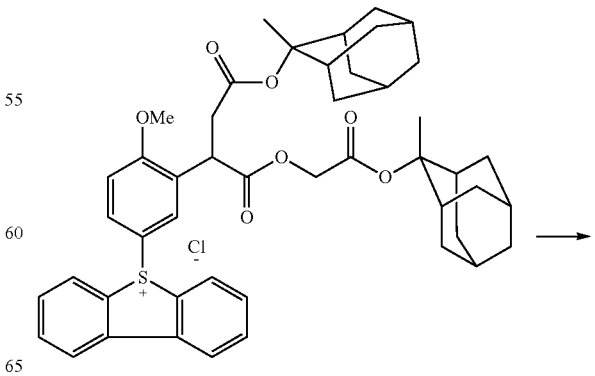

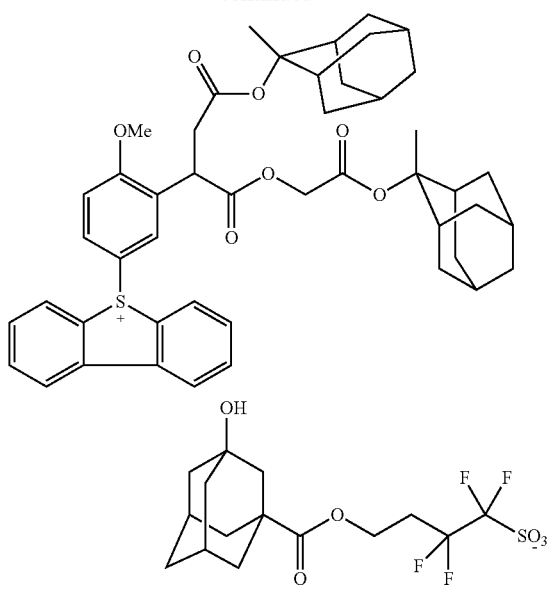

5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1,2,2-tetrafluoro-4-((3-hydroxyadamantane-1-carbonyl)oxy)butane-1-sulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (25.0 g, 31.4 mmol) and sodium 3-hydroxyadamantane-acetoxy-1,1,2,2-tetrafluorobutane-1-sulfonate (13.5 g, 31.7 mmol) were dissolved in DCM (200 mL) and water (200 mL) and stirred at 25° C. overnight. The layers were separated, the aqueous phase extracted with dichloromethane (100 mL), the combined organic layers washed with water (10×200 mL) and concentrated under reduced pressure to afford the title compound (31.6 g, 86%) as a white solid. $^1$H NMR (300 MHz, (CD$_3$)$_2$CO) δ: 8.56 (dd, J=7.8, 2.1 Hz, 2H), 8.37 (d, J=8.1 Hz, 1H), 8.30 (d, J=7.8 Hz, 1H), 8.00-8.10 (m, 2H), 7.76-7.88 (m, 3H), 7.60 (dd, J=10, 2.7 Hz, 1H), 7.31 (d, J=10 Hz, 1H), 5.62 (s, 2H), 4.53-4.69 (m, 2H), 4.45 (dd, J=8.7, 6.6 Hz, 1H), 4.31 (t, J=6.6 Hz, 2H), 3.96 (s, 3H), 3.63 (s, 10H), 2.98-3.08 (m, 1H), 2.61-2.79 (m, 3H), 1.40-2.23 (m, 48H).

EXAMPLE 9

5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (37.8 g, 47.4 mmol and N,N,N-trimethyl-1-phenylmethanaminium 1,1-difluoro-2-(methacryloyloxy)ethanesulfonate (18.9 g, 49.8 mmol) were dissolved in DCM (250 mL) and water (250 mL) and stirred at 25° C. overnight. The layers were separated, the aqueous phase extracted with dichloromethane (100 mL), the combined organic layers washed with water (8×200 mL) and concentrated under reduced pressure to afford the title compound (36.0, 77%) as an off white solid. $^1$H NMR (500 MHz, (CD$_3$)$_2$CO) 6: (8.52-8.56 (m, 2H), 8.37 (d, J=8 Hz, 1H), 8.31 (d, J=8.5 Hz, 1H), 7.99-8.06 (m, 2H), 7.78-7.85 (m, 3H), 7.63 (dd, J=9, 1.5 Hz, 1H), 7.31 (d, J=9 Hz, 1H), 6.16-6.19 (m, 1H), 5.64-6.69 (m, 1H), 5.62 (s, 2h), 4.72-4.79 (m, 2H), 4.50-4.65 (m, 2H), 4.42-4.47 (m, 1H), 3.96 (s, 3H), 2.99-3.07 (m, 1H), 2.63-2.70 (m, 1H), 2.10-2.30 (m, 4H), (1.42-2.09 (m, 31H).

EXAMPLE 10

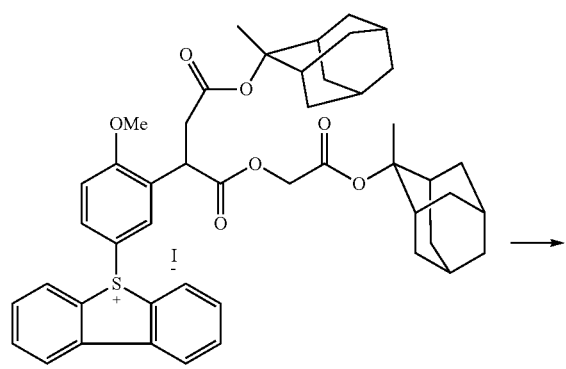

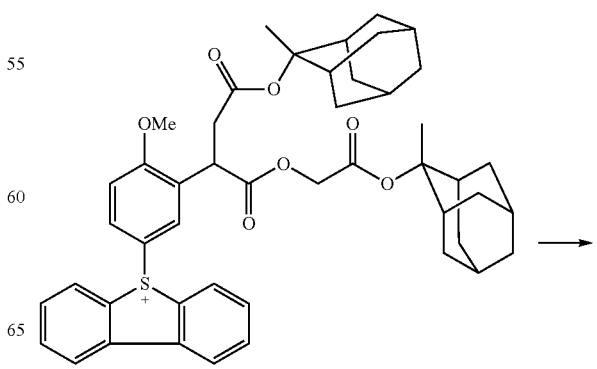

-continued

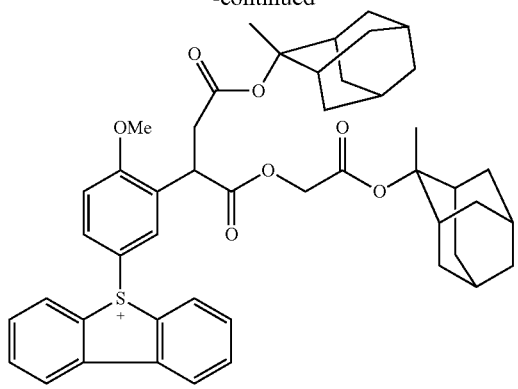

EXAMPLE 11

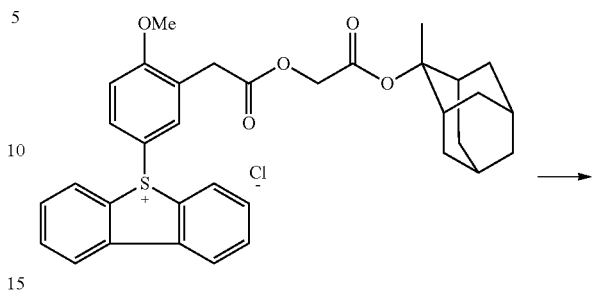

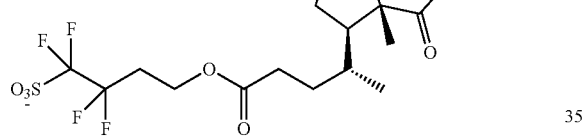

5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 4-(((4R)-4-(10,13-dimethyl-3,7,12-trioxohexadecahydro-1H-cyclopentaphenanthren-17-yl)pentanoyl)oxy)-1,1,2,2-tetrafluorobutane-1-sulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (15.0 g, 18.8 mmol) and sodium 4-(((4R)-4-(10,13-dimethyl-3,7,12-trioxohexadecahydro-1H-cyclopenta[a]phenanthren-17-yl)pentanoyl)oxy)-1,1,2,2-tetrafluorobutane-1-sulfonate (12.1 g, 19.2 mmol) were dissolved in DCM (200 mL) and water (200 mL) and stirred at 25° C. overnight. The layers were separated, the aqueous phase extracted with dichloromethane (100 mL), the combined organic layers washed with water (10×200 mL) and concentrated under reduced pressure to afford the title compound (23.5 g, 91%) as a white solid. $^1$H NMR (500 MHz, (CD$_3$)$_2$CO) δ: 8.52-8.56 (m, 2H), 8.35 (d, J=8 Hz, 1H), 8.29 (d, J=8.5 Hz, 1H), 8.00-8.07 (m, 2H), 7.78-7.86 (m, 3H), 7.60 (dd, J=9, 2 Hz, 1H), 7.31 (d, J=9 Hz, 1H), 5.62 (s, 2H), 4.54-4.67 (m, 2H), 4.5 (vis t, J=11 Hz, 1H), 4.32 (t, J=7 Hz, 2H), 3.96 (s, 3H), 2.99-3.19 (m, 3H), 2.92 (t, J=6.5 Hz, 2H), 2.64-2.84 (m, 4H), 1.27-2.55 (m, 55H), 1.11 (s, 3H), 0.84 (d, J=6.5 Hz, 3H).

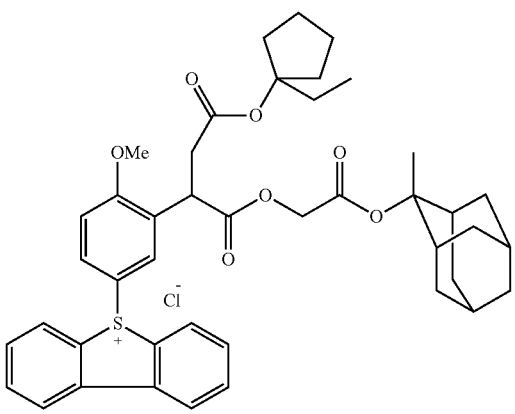

5-(3-(4-(((1-ethylcyclopentyl)oxy)-1-(2-((2-methyladamantan-2-yl)oxy)-2-oxoethoxy)-1,4-dioxobutan-2-yl)-4-methoxyphenyl)-dibenzothiophenium chloride 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (6.00 g, 10.2 mmol), 1-ethylcyclopentyl 2-chloroacetate (2.12 g, 11.2 mmol), sodium iodide (1.52 g, 10.2 mmol), and cesium carbonate (4.95 g, 15.2 mmol) were dissolved in DMF (25 mL) and stirred at 25° C. for 48 h. The reaction mixture was quenched with water (100 mL), extracted with DCM (3×100 mL), the combined organics washed with water (4×100 mL) and concentrated to a viscous oil which was precipitated into MTBE (250 mL). The crude solid was filtered and purified via silica gel flash column chromatography (neutralized TEA, eluting DCM) to afford the title compound (5.80 g, 77%) as a white solid. $^1$H NMR (300 MHz, (CD$_3$)$_2$CO) δ: 8.50-8.58 (m, 3H), 8.42 (d, J=7.8 Hz, 1H), 7.98-8.07 (m, 2H), 7.88 (d, J=2.4 Hz, 1H), 7.76-7.86 (m, 2H), 7.67 (dd, J=10, 2.1 Hz, 1H), 7.29 (d, J=10 Hz, 1H), 4.54-4.90 (m, 4H), 4.44 (dd, J=8.7, 6 Hz, 1H), 3.96 (s, 3H), 3.81 (q, J=7.2 Hz, 2H), 2.94-3.04 (m, 1H), 2.61 (dd, J=16.5, 5.8 Hz, 1H), 2.21-2.28 (m, 2H), 1.51-2.10 (m, 13 H), 1.46 (t, J=6 Hz, 2H), 1.31 (s, 3H), 0.82-0.95 (m, 4H), 0.77 (t, J=6 Hz, 3H).

EXAMPLE 12

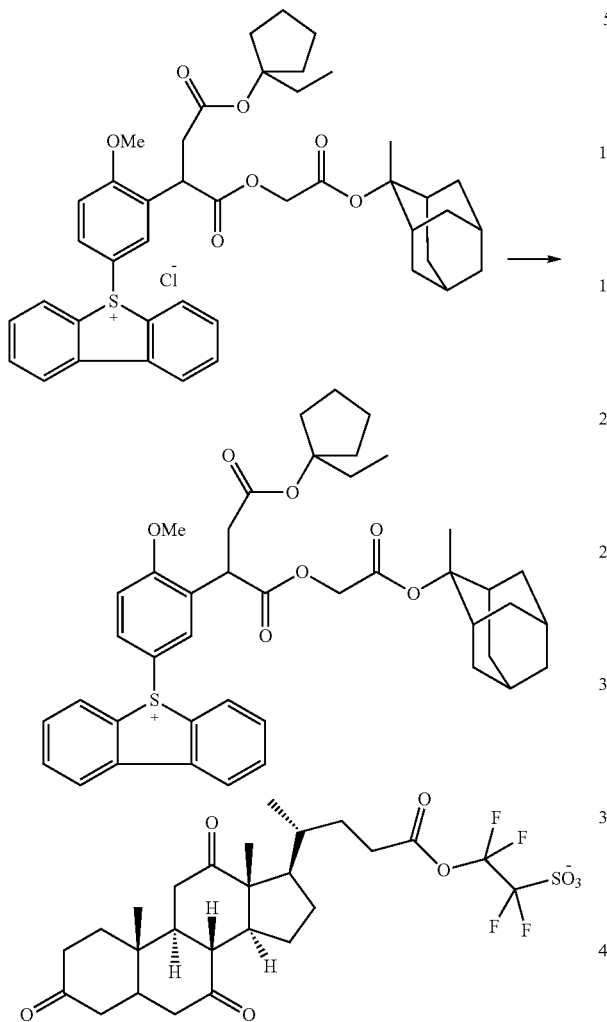

5-(3-(4-((1-ethylcyclopentyl)oxy)-1-(2-((2-methyl-adamantan-2-yl)oxy)-2-oxoethoxy)-1,4-dioxobutan-2-yl)-4-methoxyphenyl)dibenzothiophen-5-ium 4-(((4R)-4-(10,13-dimethyl-3,7,12-trioxohexadeca-hydro-1H-cyclopenta[a]phenanthren-17-yl)pen-tanoyl)oxy)-1,1,2,2-tetrafluorobutane-1-sulfonate 5-(3-(4-((1-ethylcyclopentyl)oxy)-1-(2-((2-methylada-mantan-2-yl)oxy)-2-oxoethoxy)-1,4-dioxobutan-2-yl)-4-methoxyphenyl)-dibenzothiophenium chloride (2.50 g, 3.35 mmol) and sodium 4-(((4R)-4-(10,13-dimethyl-3,7,12-tri-oxohexadecahydro-1H-cyclopenta[a]phenanthren-17-yl)pentanoyl)oxy)-1,1,2,2-tetrafluorobutane-1-sulfonate (2.23 g, 3.52 mmol) were dissolved in DCM (50 mL) and water (50 mL) and stirred at 25° C. overnight. The layers were separated, the aqueous phase extracted with dichlorometh-ane (50 mL), the combined organic layers washed with water (7×75 mL) and concentrated under reduced pressure to afford the title compound (3.47 g, 78%) as a white solid. $^1$H NMR (300 MHz, (CD$_3$)$_2$CO) δ: 8.51-8.57 (m, 2h0, 8.36 (d, J=8.1 Hz, 1H), 8.28 (d, J=8.1 Hz, 1H), 8.00-8.08 (m, 2H), 7.77-7.90 (m, 3H), 7.55 (dd, J=8.7, 2.4 Hz, 1H), 7.31 (d, J=2.4 Hz, 1H0, 4.52-4.70 (m, 2 H), 4.41-4.48 (m, 3H), 4.32 (t, J=6.9 Hz, 2H), 3.96 (s, 3H), 3.77 (q, J=7.2 Hz, 2H), 2.20-3.20 (m, 15 H), 1.23-2.15 (m, 41H), 1.11 (s, 3H), 0.82-0.95 (m, 3H), 0.77 (t, J=7.2 Hz, 3H).

EXAMPLE 13

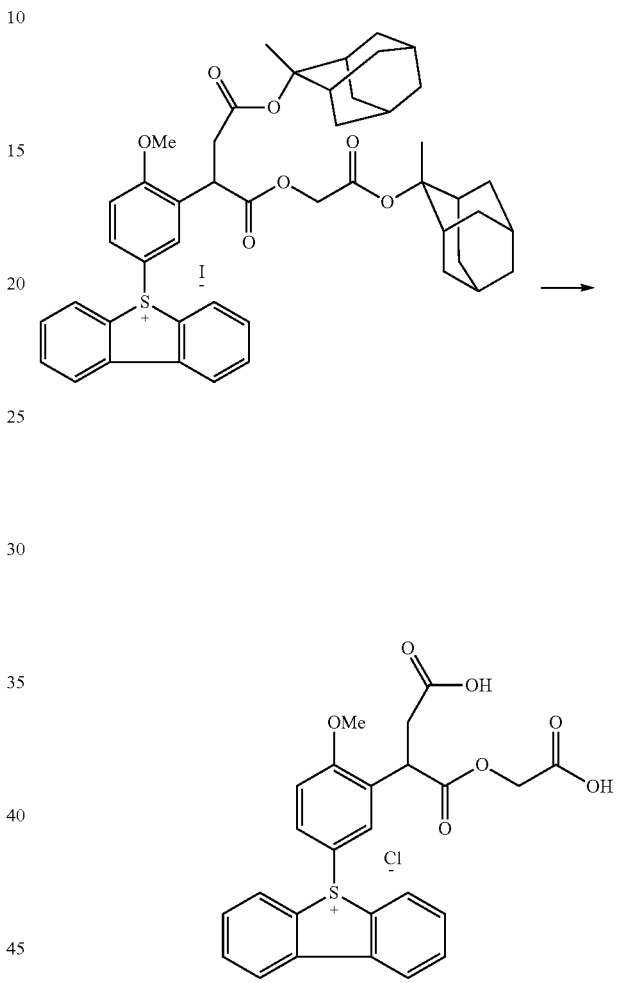

5-(3-(3-carboxy-1-(carboxymethoxy)-1-oxopropan-2-yl)-4-methoxyphenyl)-5H-dibenzo[b,d]thiophen-5-ium chloride Triflic acid (0.5 mL) was added to a solution of 5-(3-(4-((1-ethylcyclopentyl)oxy)-1-(2-((2-methyladamantan-2-yl)oxy)-2-oxoethoxy)-1,4-dioxobutan-2-yl)-4-methoxyphe-nyl)-dibenzothiophenium chloride (7.00 g, 8.87 mmol) in DCM (50 mL) and stirred at 25° C. overnight. The white precipitate was filtered off, washed with DCM (2×20 mL) and MTBE (2×200 mL) to afford the title compound (4.05 g, 92%) as a white solid. $^1$H NMR (500 MHz, (CD$_3$)$_2$SO) δ: 12.0-13.0 (brs, 2COOH), 8.48-8.52 (m, 2H), 8.31 (d, J=8 Hz, 1H), 8.24 (d, J=7.5 Hz, 1H), 7.92-7.97 (m, 2H), 7.70-7.77 (m, 3H), 7.12-7.24 (m, 2H), 4.54 (vis d, J=4 Hz, 2H), 4.31-4.34 (m, 1H), 3.82 (s, 3H), 2.90 (dd, J=17, 9 Hz, 1H), 2.52 (dd, J=15, 3.5 Hz, 1H).

EXAMPLE 14

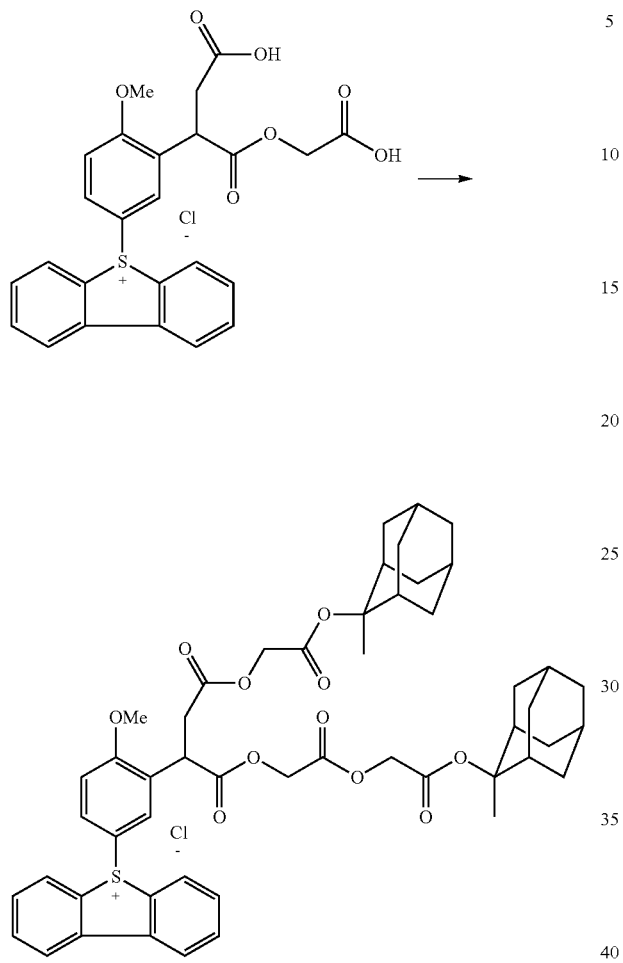

5-(4-methoxy-3-(4-(2-((2-methyladamantan-2-yl)oxy)-2-oxoethoxy)-1-(2-(2-((2-methyladamantan-2-yl)oxy)-2-oxoethoxy)-2-oxoethoxy)-1,4-dioxobutan-2-yl)phenyl)-dibenzothiophenium chloride 5-(3-(3-carboxy-1-(carboxymethoxy)-1-oxopropan-2-yl)-4-methoxyphenyl)-dibenzothiophenium chloride (4.00 g, 8.00 mmol), 2-methyladamantan-2-yl 2-chloroacetate (4.07 g, 16.8 mmol), sodium iodide (2.4 g, 16.0 mmol) and cesium carbonate (6.51 g, 20 mmol) were dissolved in DMF (60 mL) and vigorously stirred at 25° C. for 48 h. The reaction mixture was quenched with water (200 mL) and extracted with DCM (3×100 mL). The combined organic layers were washed with water (4×200 mL), concentrated to a viscous oil and precipitated from MTBE (300 mL) to provide a solid residue which was further purified via silica gel flash column chromatography (neutralized TEA, eluting DCM) to afford the title compound (2.52 g, 35%) as an off-white solid. $^1$H NMR (500 MHz, (CD3)2CO) δ: 8.52-8.56 (m, 2H), 8.47 (d, J=8.5 Hz, 1H), 8.38 (d, J=8 Hz, 2H), 7.99-8.06 (m, 2H), 7.92 (d, J=2 Hz, 1H), 7.77-7.85 (m, 2H), 7.62 (dd, J=9, 2 Hz, 1H), 7.29 (d, J=9 Hz, 1H), 4.50-4.71 (m, 6H), 4.45-4.49 (m, 1H), 3.96 (s, 3H), 3.14-3.22 (m, 1H), 2.74-2.81 (m, 1H), 1.50-2.33 (m, 30H), 1.13 (s, 3H), 1.13 (s, 3H).

EXAMPLE 15

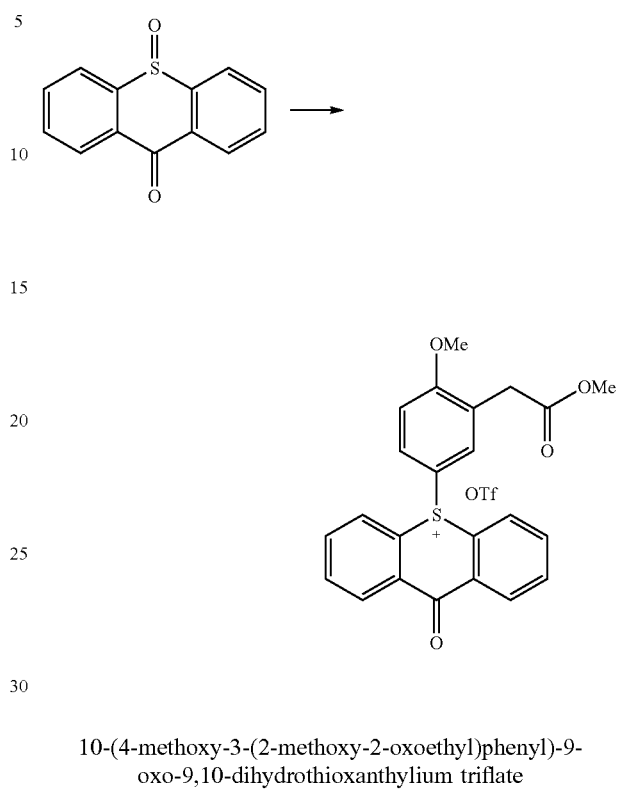

10-(4-methoxy-3-(2-methoxy-2-oxoethyl)phenyl)-9-oxo-9,10-dihydrothioxanthylium triflate Triflic acid (7.3 mL, 43.4 mmol) was added dropwise to a solution of thioxanthone oxide (5.00 g, 21.7 mmol) and methyl 2-(2-methoxyphenyl)acetate (4.31 g, 23.9 mmol) in DCM (60 mL) at −78° C. and slowly warmed to 25° C. overnight. The reaction mixture was quenched with water (100 mL), the layers separated, and the aqueous phase washed with water (4×100 mL) and concentrated to a crude solid. The crude solid was dissolved in minima acetone, precipitated into MTBE (1 L), and filtered to afford the title compound (10.0 g, 85%) as a white solid. $^1$H NMR (500 MHz, (CD3)2CO) δ: 8.66-8.69 (m, 2H), 8.19-8.22 (m, 3H), 8.10-8.13 (m, 4H), 7.91 (d, J=2.5 Hz, 1H), 7.37 (d, J=9 Hz, 1H), 3.96 (s, 3H), 3.61 (s, 2H), 3.57 (s, 3H).

EXAMPLE 16

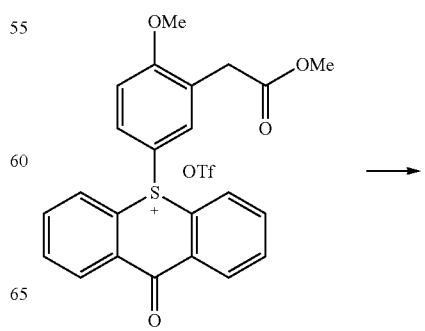

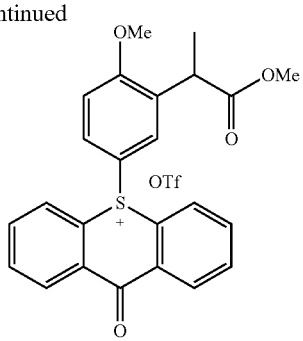

10-(4-methoxy-3-(1-methoxy-1-oxopropan-2-yl)
phenyl)-9-oxo-9,10-dihydrothioxanthylium triflate 10-(4-methoxy-3-(2-methoxy-2-oxoethyl)phenyl)-9-oxo-9,10-dihydrothioxanthylium triflate (3.00 g, 5.55 mmol), methyl iodide (3.9 g, 27.7 mmol), and cesium carbonate (3.6 g, 11.1 mmol) were dissolved in DMF (25 mL) and stirred at 25° C. for 4 h. The reaction mixture was diluted with water (100 mL) and extracted with DCM (2×75 mL). The combined organics were washed with water (4×100 mL) and concentrated to a viscous oil which was precipitated from MTBE (400 mL) and filtered to afford the title compound (2.35 g, 64%) as a light orange solid. 1H NMR (500 MHz, (CD3)2CO) δ: 8.62-8.66 (m, 2H), 8.29-8.33 (m, 2H), 8.06-8.12 (m, 5H), 8.03 (d, J=2, 1H), 7.34 (d, J=9 Hz, 1H), 3.99 (q, J=7.5 Hz, 1H), 3.94 (s, 3H), 3.55 (s, 3H), 1.35 (d, J=7.5 Hz, 3H).

EXAMPLE 17

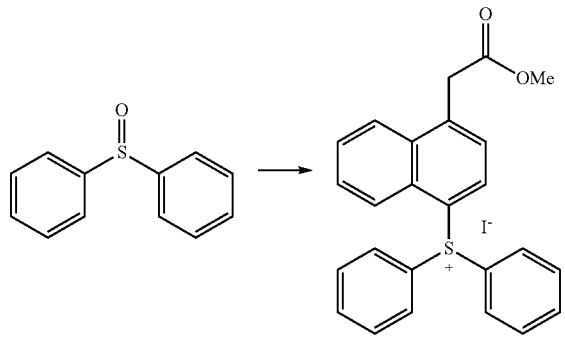

(4-(2-methoxy-2-oxoethyl)naphthalen-1-yl)diphenyl-sulfonium iodide

Triflic anhydride (16.6 mL, 0.099 mmol) was added dropwise to a solution of diphenylsulfoxide (10.0 g, 49.4 mmol) and methyl 2-(naphthalen-1-yl)acetate (10.9 g, 54.5 mmol) in DCM (100 mL) at −78° C. and stirred for 3 h. The reaction was quenched by the slow addition of water (50 mL) and slowly warmed to r.t. The layers were separated and the organic layer washed with 2M aqueous sodium iodide (10×100 mL), and water (3×100 mL), then concentrated to a viscous oil which was precipitated from MTBE (600 mL) to afford the title compound (18.7 g, 74%) as a light brown hydroscopic solid. 1H NMR (500 MHz, (CD3)2CO) δ: 8.48-8.51 (m, 1H), 8.30-8.33 (m, 1H), 8.03-8.10 (m, 3H), 7.75-7.99 (m, 8H), 7.72 (d, J=8 Hz, 1H). 4.39 (s, 2H), 3.68 (s, 3H).

EXAMPLE 18

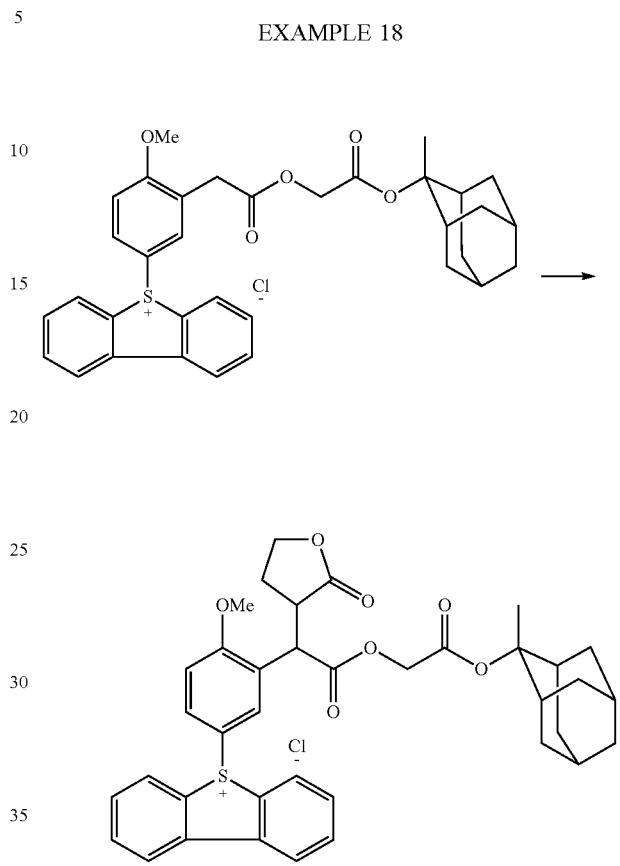

5-(4-methoxy-3-(2-(2-((2-methyladamantan-2-yl)
oxy)-2-oxoethoxy)-2-oxo-1-(2-oxotetrahydrofuran-
3-yl)ethyl)phenyl)-dibenzothiophenium chloride 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (6.00 g, 10.2 mmol), (R,S)-3-bromodihydrofuran-2(3H)-one (1.84 g, 11.2 mmol), and cesium carbonate (4.95 g, 15.2 mmol) were dissolved in DMF (25 mL) and stirred at 25° C. for 24 h. The reaction mixture was diluted with water (100 mL) and extracted with DCM (2×50 mL). The combined organic layers were washed with water (4×75 mL) and concentrated to a viscous oil which was precipitated into MTBE (500 mL) and filtered. The crude solid was purified via silica gel flash column chromatography to afford the title compound as a mixture of diasteriomers (5.54 g, 71%) as a brown solid which can be further purified via recrystallization from acetone to afford the title compound (2.71 g, 35%) as a white solid. $^1$H NMR (500 MHz, (CD3)2CO) δ: 8.43-8.52 (m, 2H), 8.32 (d, J=8 Hz, 1H), 8.23 (dd, J=19, 8 Hz, 1H), 7.92-7.96 (m, 2H), 7.71-7.74 (m, 2H), 7.65 (d, J=9.5 Hz, 1H), 7.24-7.39 (m, 1H), 7.18-7.23 (m, 1H), 5.57 (s, 2H), 4.49 (d, J=5 Hz, 1H), 4.31 (t, J=7.5 Hz, 1H), 4.23 (d, J=7 Hz, 1H), 4.07-4.15 (m, 2H), 3.81 (d, J=13 Hz, 3H), 3.39-3.44 (m, 1H), 3.12-3.15 (m, 1), 1.32-2.27 (m, 17H).

EXAMPLE 19

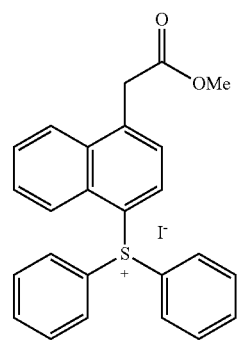

(4-(1-methoxy-4-(2-methoxyethoxy)-1-oxobutan-2-yl)naphthalen-1-yl)diphenylsulfonium iodide (4-(2-methoxy-2-oxoethyl)naphthalen-1-yl)diphenylsulfonium iodide (5.00 g, 9.76 mmol), 1-bromo-2-(2-methoxyethoxy)ethane (1.96 g, 10.7 mmol), sodium iodide (2.93 g, 19.5 mmol), and cesium carbonate (6.34 g, 19.5 mmol) are dissolved in DMF (40 mL) and stirred a 25° C. for 24 h. The reaction mixture is quenched with water (100 mL), extracted with DCM (2×75 mL), the combined organic layers washed with water (4×100 mL), concentrated to a viscous oil, precipitated from MTBE (750 mL) and filtered. The crude mixture is further purified via silica gel flash column chromatography (neutralized TEA, eluting DCM) to afford the title compound as a white solid.

EXAMPLE 20

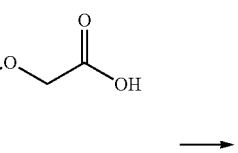
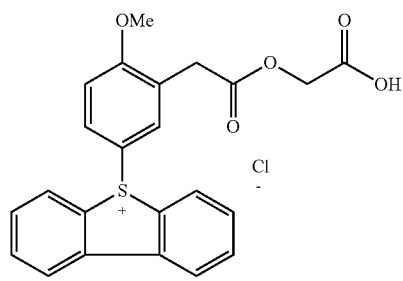

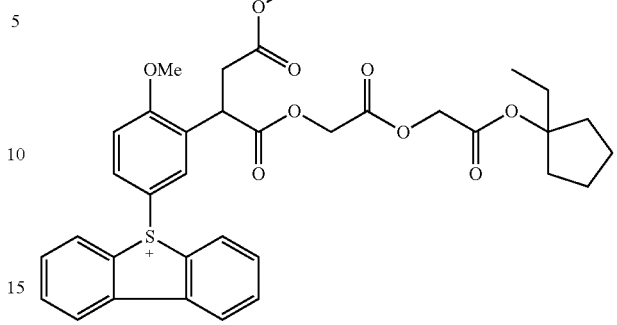

5-(3-(4-((1-ethylcyclopentyl)oxy)-1-(2-(2-((1-ethylcyclopentyl)oxy)-2-oxoethoxy)-2-oxoethoxy)-1,4-dioxobutan-2-yl)-4-methoxyphenyl)dibenzothiophenium chloride 5-(3-(2-(carboxymethoxy)-2-oxoethyl)-4-methoxyphenyl)-dibenzothiophenium chloride (5.00 g, 11.8 mmol), 1-ethylcyclopentyl 2-chloroacetate (4.98 g, 26.0 mmol), sodium iodide (3.54 g, 23.6 mmol), and cesium carbonate (11.5 g, 35.4 mmol) are dissolved in DMF (50 mL) and stirred at 25° C. for 48 h. The reaction mixture is quenched with water (100 mL), extracted with DCM (2×75 mL), the combined organic layers washed with water (4×100 mL), concentrated to a viscous oil, precipitated from MTBE (750 mL) and filtered. The crude mixture is further purified via silica gel flash column chromatography (neutralized TEA, eluting DCM) to afford the title compound as a white solid.

EXAMPLE 21

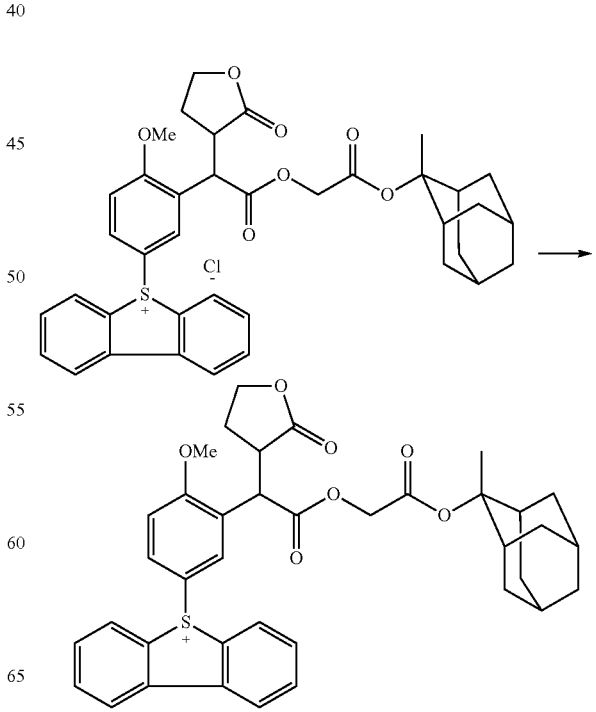

-continued

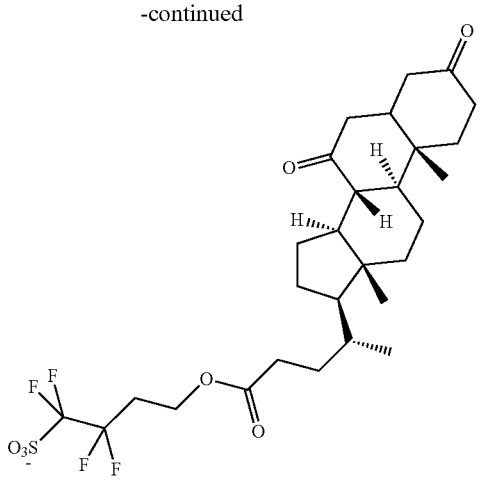

5-(4-methoxy-3-(2-(2-(2-methyladamantan-2-yl)
oxy)-2-oxoethoxy)-2-oxo-1-(2-oxotetrahydrofuran-
3-yl)ethyl)phenyl)-dibenzothiophenium 4-(((4R)-4-
(10,13-dimethyl-3,7,12-trioxohexadecahydro-1H-
cyclopentaphenanthren-17-yl)pentanoyl)oxy)-1,1,2,
2-tetrafluorobutane-1-sulfonate 5-(4-methoxy-3-(2-(2-((2-methyladamantan-2-yl)oxy)-2-oxoethoxy)-2-oxo-1-(2-oxotetrahydrofuran-3-yl)ethyl)phenyl)-dibenzothiophenium chloride (10 g, 14.8 mmol) and sodium 4-(((4R)-4-(10,13-dimethyl-3,7,12-trioxohexadecahydro-1H-cyclopentaphenanthren-17-yl)pentanoyl)oxy)-1,1,2,2-tetrafluorobutane-1-sulfonate (9.86 g, 15.6 mmol) are dissolved in DCM (250 mL) and water (250 mL) and stirred at 25° C. overnight. The layers are separated, the organic layer washed with water (10×200 mL), and concentrated under reduced pressure to afford the title compound as a white solid.

EXAMPLE 22

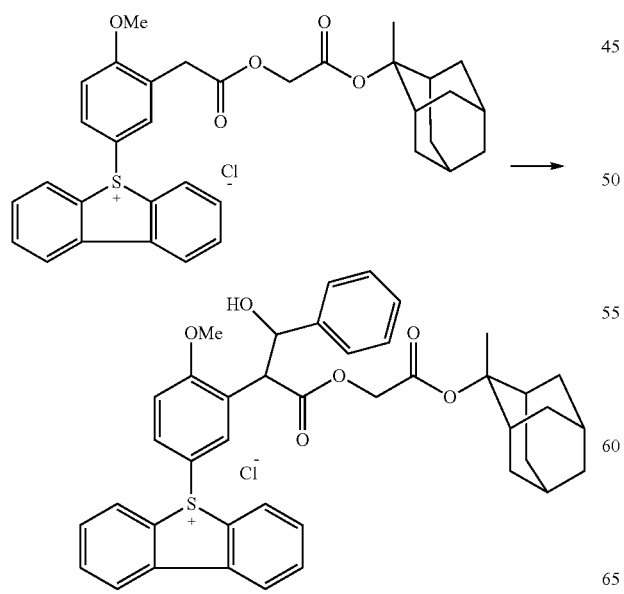

5-(3-(1-hydroxy-3-(2((2-methyladamantan-2-yl)oxy)-2-oxoethoxy)-3-oxo-1-phenylpropan-2-yl)-4-methoxyphenyl)-dibenzothiophenium chloride Pentanal (1.53 g, 17.8 mmol) in DMF (15 mL) is slowly added to a stirring solution of 5-(4-methoxy-3-(2-(2-((2-methyladamantan-2-yl)oxy)-2-oxoethoxy)-2-oxoethyl)phenyl)-dibenzothiophenium chloride (10 g, 16.9 mmol) and cesium carbonate (11.0 g, 33.8 mmol) in DMF (60 mL) at 0° C. After full addition the reaction mixture is warmed to 25° C. and stirred for 18 h. The resulting solution is quenched with water (200 mL), extracted with DCM (2×150 mL), the combined organic layers washed with water (4×200 mL), concentrated to a viscous oil, precipitated from MTBE (1 L) and filtered. The crude mixture is further purified via silica gel flash column chromatography (neutralized TEA, eluting DCM) to afford the title compound as a white solid.

EXAMPLE 23

Preparation of Polymer with Acid Generator Units

Heel solution was made by dissolving 2-phenylpropan-2-yl methacrylate (0.39 g), 2-oxotetrahydrofuran-3-yl methacrylate (0.33 g), 3,5-bis(1,1,1,3,3,3-hexafluoro-2-hydroxy-propan-2-yl)cyclohexyl methacrylate (0.57 g) and 5-(4-(2-(1-methylcyclopentyloxy)-2-oxoethoxy)-3,5-dimethylphenyl)-5H-dibenzo[b,d]thiophenium 1,1-difluoro-2-(methacryloyloxy)ethanesulfonate (0.31 g) in 12.81 g acetonitrile/tetrahydrofuran (2/1 v/v). Feed solution was prepared by dissolving 2-phenylpropan-2-yl methacrylate (185.54 g, 0.967 mol), 2-oxotetrahydrofuran-3-yl methacrylate (204.27 g, 1.26 mol), 3,5-bis(1,1,1,3,3,3-hexafluoro-2-hydroxypropan-2-yl)cyclohexyl methacrylate (127.98 g, 0.29 mol) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (81.5 g, 0.132 mol) in 606 g ethyl lactate:γ-butryl lactone (30/70 v/v). Initiator solution was prepared by dissolving 65.96 g initiator (V-65) in 66 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (2.0 g). The contents were cooled to room temperature and precipitated twice out of 10×(by weight) IPE/MeOH 95/5 (w/w). The polymer obtained was dried in vacuuo after each precipitation step at 50° C. for 24 hours to yield 500 g polymer.

EXAMPLE 24

Preparation of Polymer with Acid Generator Units

The same process used for Example 23 was used in the preparation of polymer, except 5-phenyl-5H-dibenzo[b,d]thiophenium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate.

EXAMPLE 25

Preparation of Polymer with Acid Generator Units

The same process used for Example 23 was used in the preparation of polymer, except 5-(4-(tert-butyl)phenyl)-5H-dibenzo[b,d]thiophen-5-ium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy) ethanesulfonate.

EXAMPLE 26

Preparation of Polymer with Acid Generator Units

The same process used for Example 23 was used in the preparation of polymer, except the monomer of example 9 was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate.

EXAMPLE 27

Preparation of Polymer with Acid Generator Units
(Low PPMA as TBP-F2)

The same process used for Example 23 was used in the preparation of polymer, except 5-(4-(tert-butyl)phenyl)-5H-dibenzo[b,d]thiophen-5-ium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy) ethanesulfonate, and 10 mol % less 2-phenylpropan-2-yl methacrylate was used and replaced by 2-oxotetrahydrofuran-3-yl methacrylate.

EXAMPLE 28

Further Preparation and Processing of Photoresist Composition

A positive-tone photoresist composition was prepared by combining component 1, 7.952 g of a 10 wt % solution of the polymer from Example 10 in ethyl lactate; component 2, 9.289 g of a 2 wt % solution of the acid generator 5-(4-(2-(1-ethylcyclopentyloxy)-2-oxoethoxy)-3,5-dimethylphenyl)-5H-dibenzo[b,d]thiophenium 3-hydroxyadamantane-acetoxy-1,1,2,2-tetrafluorobutane-1-sulfonate in ethyl lactate; component 3, 0.932 g of a 0.5 wt % solution of tetrakis(2-hydroxypropyl)ethylenediamine in ethyl lactate; component 4, 0.680 g of a 2 wt % solution of (1r,3s,5R,7S)-3-hydroxyadamantane-1-carboxylic acid, 5-(4-(2-((1-ethylcyclopentyl)oxy)-2-oxoethoxy)-3,5-dimethylphenyl)-5H-dibenzo[b,d]thiophen-5-ium salt in ethyl lactate; component 5, 0.159 g of a 0.5 wt % solution of fluorinated surfactant (Omnova PF656) in ethyl lactate; component 6, 9.287 g of ethyl lactate; and component 7, 11.700 g of 2-hydroxyisobutyric acid methyl ester. The formulated resist was passed through a 0.01 µm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Examples 29-41

Photoresist Compositions

Photoresist compositions were prepared and processed according to Example 28 with the appropriate changes according to Table 1:

TABLE 1

| | Photoresist components: | | | | | | |
|---|---|---|---|---|---|---|---|
| Example: | Component 1 | Component 2 | Component 3 | Component 4 | Component 5 | Component 6 | Component 7 |
| 29 | Example 23 [55.432] | [94.235] | [13.304] | | [1.109] | [48.170] | [87.750] |
| 30 | Example 24 [10.322] | 2-1 [10.071] | [0.614] | 2-2 [0.619] | [0.206] | [13.543] | [14.625] |
| 31 | Example 25 [9.378] | Example 8 [14.794] | [0.563] | 2-3 [0.626] | [0.188] | [10.386] | [14.065] |
| 32 | Example 25 [9.389] | Example 8 [14.811] | [0.563] | 2-2 [0.558] | [0.188] | [9.866] | [14.625] |
| 33 | Example 26 [5.333] | Example 8 [10.373] | [0.320] | 2-3 [0.356] | [0.107] | [4.737] | [8.775] |
| 34 | Example 25 [5.371] | Example 8 [10.175] | [0.322] | 2-4 [0.359] | [0.107] | [4.887] | [8.775] |
| 35 | Example 25 [6.425] | Example 8 [4.819] | [0.385] | 2-3 [0.429] | [0.128] | [9.039] | [8.775] |
| 36 | Example 25 [7.482] | Example 8 [11.802] | [0.449] | [0.640] | [0.150] | [7.778] | [11.700] |
| 37 | Example 25 [7.201] | Example 10 [13.369] | [0.432] | 2-3 [0.481] | [0.144] | [6.673] | [11.700] |
| 38 | Example 27 [7.506] | Example 8 [11.841] | [0.360] | 2-3 [0.501] | [0.150] | [7.942] | [11.700] |
| 39 | Example 25 [7.275] | Example 12 [12.993] | [0.437] | 2-3 [0.486] | [0.246] | [6.964] | [11.700] |
| 40 | Example 23 [7.238] | 2-5 [13.231] | 2-6 [2.171] | | [0.145] | [14.675] | [12.539] |
| 41 | Example 23 [6.439] | Example 10 [17.415] | 2-6 [1.429] | | [0.129] | [9.888] | [14.700] |

In Table 1, the referenced characters indicate the following according to Table 2 with values in brackets [ ] indicating the amount in grams of the component added in accordance with Example 28 or are direct references to synthetic examples, again with values in brackets [ ] indicating the amount in grams of the component added in accordance with Example 28. When there are no reference characters or corresponding examples, the component is the same as the corresponding component of Example 28. All samples were processed according to Example 28.

TABLE 2

Key for Table 1:

| Character | Name |
|---|---|
| 2-1 | 5-(4-(tert-butyl)phenyl)-5H-dibenzo[b,d]thiophen-5-ium 1,1,2,2-tetrafluoro-4-(((1r,3s,5R,7S)-3-hydroxyadamantane-1-carbonyl)oxy)butane-1-sulfonate |
| 2-2 | (1r,3s,5R,7S)-3-hydroxyadamantane-1-carboxylic acid, 5-phenyl-5H-dibenzo[b,d]thiophen-5-ium salt |
| 2-3 | (1r,3s,5R,7S)-3-hydroxyadamantane-1-carboxylic acid, 5-(4-(tert-butyl)phenyl)-5H-dibenzo[b,d]thiophen-5-ium salt |
| 2-4 | 5-(4-(tert-butyl)phenyl)-5H-dibenzo[b,d]thiophen-5-ium (4R)-4-(((8R,9S,10S,13R,14S,17R)-10,13-dimethyl-3,7,12-trioxohexadecahydro-1H-cyclopenta[a]phenanthren-17-yl)pentanoate |
| 2-5 | 5-(4-(tert-butyl)phenyl)-5H-dibenzo[b,d]thiophen-5-ium 4-(((4R)-4-((8R,9S,10S,13R,14S,17R)-10,13-dimethyl-3,7,12-trioxohexadecahydro-1H-cyclopenta[a]phenanthren-17-yl)pentanoyl)oxy)-1,1,2,2-tetrafluorobutane-1-sulfonate |
| 2-6 | 1,1',1''-nitrilotris(propan-2-ol) |

EXAMPLE 42

Lithographic Evaluation

For the tables below, Esize, CDU, and EL % are all evaluated in the following way: Comparative Examples are normalized to 1 and consequently designated with "◊"; very good metrics, those which represents at least a 20% improvement relative to the respective comparative, are designated with "Δ"; good metrics, those which represents at least a 10% improvement relative to the respective comparative, are designated with "□"; improved metrics, those which represents between 0% and 10% improvement relative to the respective comparative, are designated with "■"; similar metrics, those which represent between <0% and −5% improvement relative to the respective comparative, are designated with "●"; and underperformance is marked with "○".

E-size and exposure latitude % (EL %) were calculated from critical dimension (CD) data through dose and focus (FEM) with 10% CD boundaries restricted to 100 nm depth of focus (DoF). CDU is the calculated 3 Sigma for 10 FOV measuring 36 CH for each FOV, all taken within best exposure/best focus.

TABLE 3

30 nm CH data. Normalized numbers below 1 indicate an improvement over the comparative for Esize, DCU and CER. Normalized numbers over 1 indicate an improvement over the comparative for EL

| Example | Esize (mJ) | CDU (nm) | CER (nm) | EL % |
|---|---|---|---|---|
| 28 (comparative) | ◊ | ◊ | ◊ | ◊ |
| 31 | ● | Δ | ○ | ■ |

TABLE 3-continued 30 nm CH data. Normalized numbers below 1 indicate an improvement over the comparative for Esize, DCU and CER. Normalized numbers over 1 indicate an improvement over the comparative for EL

| Example | Esize (mJ) | CDU (nm) | CER (nm) | EL % |
|---|---|---|---|---|
| 32 | ■ | Δ | ○ | ○ |
| 33 | ○ | Δ | ● | ■ |
| 34 | ○ | □ | ● | Δ |
| 35 | □ | ■ | ■ | ○ |
| 36 | ● | Δ | ● | ■ |
| 37 | ○ | ■ | ● | ○ |
| 38 | ○ | Δ | ● | ○ |
| 39 | ■ | ■ | ● | ● |

TABLE 4

30 nm CH data. Normalized numbers below 1 indicate an improvement over the comparative for Esize, DCU and CER. Normalized numbers over 1 indicate an improvement over the comparative for EL

| Example | Esize (mJ) | CDU (nm) | CER (nm) | EL % |
|---|---|---|---|---|
| 29 (comparative) | ◊ | ◊ | ◊ | ◊ |
| 31 | □ | Δ | ● | ■ |
| 32 | Δ | Δ | ○ | ○ |
| 33 | □ | ■ | ■ | ■ |
| 34 | □ | ■ | ■ | Δ |
| 35 | Δ | ● | □ | ● |
| 36 | ■ | Δ | ● | ● |
| 37 | ■ | ● | ■ | ○ |
| 38 | □ | Δ | ■ | ○ |
| 39 | □ | ● | □ | ● |

TABLE 5

30 nm CH data. Normalized numbers below 1 indicate an improvement over the comparative for Esize, DCU and CER. Normalized numbers over 1 indicate an improvement over the comparative for EL

| Example | Esize (mJ) | CDU (nm) | CER (nm) | EL % |
|---|---|---|---|---|
| 30 (comparative) | ◊ | ◊ | ◊ | ◊ |
| 31 | ○ | Δ | ○ | ■ |
| 32 | ■ | Δ | ○ | ● |
| 33 | ○ | ■ | ○ | ■ |
| 34 | ○ | ■ | ○ | Δ |
| 35 | Δ | ● | ■ | ● |
| 36 | ○ | Δ | ○ | ● |
| 37 | ○ | ● | ● | ● |
| 38 | ○ | Δ | ● | ● |
| 39 | ■ | ● | ● | ● |

TABLE 6

26 nm LS data. Normalized numbers below 1 indicate an improvement in Esize.

| Example | 26 nm LS Esize (mJ) |
|---|---|
| 39 (comparative) | ◊ |
| 29 (comparative) | ● |
| 41 | □ |

As seen in Tables 3-6, photoresists that comprise a photoacid generator (PAG) of the invention exhibit improved lithographic performance.

What is claimed is:

1. A photoresist composition that comprises an acid generator that comprises a structure of Formula (I):a

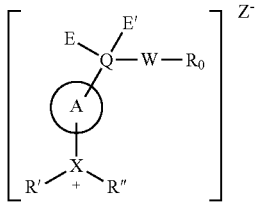

wherein Z is a counter anion;

X is sulfur or iodine;

$R_0$ is hydrogen or a non-hydrogen substituent;

R' and R" are the same or different non-hydrogen substituents and optionally may form a ring, provided that if X is iodine, one of R' and R" is absent;

W is —C(=O)O(CX'X")nC(=O)O—, wherein n is a positive integer and each X' and X" is independently a hydrogen or non-hydrogen substituent;

A is an optionally substituted carbocyclic aryl or optionally substituted heteroaromatic group;

Q is optionally substituted alkylene, optionally substituted alkenylene, or optionally substituted alkynylene; and E and E' are each independently hydrogen or a non-hydrogen substituent, with at least one of E and E' being a non-hydrogen substituent.

2. The photoresist composition of claim 1 wherein $Z^{31}$ is selected from the group consisting of carboxylate, sulfamate, or non-fluorinated sulfonate.

3. A method for providing a photoresist relief image, comprising:
   a) applying a coating layer of a photoresist composition of claim 2 on a substrate; and
   b) exposing the photoresist composition layer to activating radiation and developing the exposed photoresist composition coating layer.

4. The photoresist composition of claim 1 wherein $Z^{31}$ contains a polymerizable moiety.

5. A method for providing a photoresist relief image, comprising:
   a) applying a coating layer of a photoresist composition of claim 4 on a substrate; and
   b) exposing the photoresist composition layer to activating radiation and developing the exposed photoresist composition coating layer.

6. A method for providing a photoresist relief image, comprising:
   a) applying a coating layer of a photoresist composition of claim 1 on a substrate; and
   b) exposing the photoresist composition layer to activating radiation and developing the exposed photoresist composition coating layer.

7. A photoresist composition that comprises an acid generator comprising a structure of Formula (II):

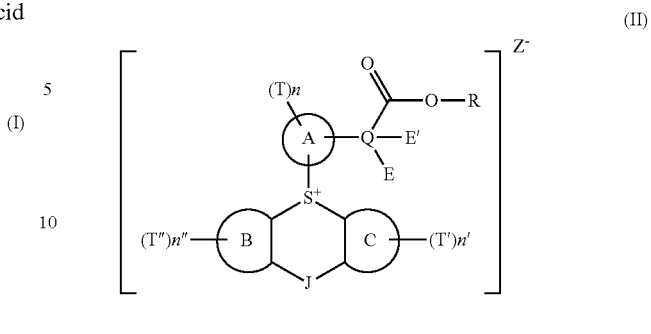

wherein Z is a counter anion;

R is —(CX'X")nC(=O)OR, wherein n is a positive integer, each X' and X" is independently a hydrogen or non-hydrogen substituent, and R' is a non-hydrogen substituent;

each T, each T' and each T" are the same or different non-hydrogen substituent, wherein either of T and T" or T and T' are capable of joining to form a ring;

n, n' and n" are each independently 0, 1, 2, 3 or 4;

J represents a chemical bond, or a group capable of covalently linking B and C;

Q is a $C_1$-$C_8$ saturated or unsaturated alkylene group;

E and E' are each independently hydrogen or a non-hydrogen substituent, with at least one of E and E' being a non-hydrogen substituent; and A, B, and C are each the same or different optionally substituted carbocyclic aryl or heteroaromatic groups.

8. A method for providing a photoresist relief image, comprising:
   a) applying a coating layer of a photoresist composition of claim 7 on a substrate; and
   b) exposing the photoresist composition layer to activating radiation and developing the exposed photoresist composition coating layer.

9. The photoresist composition of claim 7 wherein J represents a chemical bond.

10. The photoresist composition of claim 7 wherein J represents a group capable of covalently linking B and C.

11. The photoresist composition of claim 10 wherein J is optionally substituted alkylene group C=O, O, SO, $SO_2$, NH, or NR where R is a non-hydrogen substituent.

12. The photoresist composition of claim 10 wherein J is an ether, ester, amide, carbonate, sulfortate, sulforte, or sulfonamide.

13. The photoresist composition of claim 7 wherein $Z^{31}$ is selected from the group consisting of carboxylate, sulfamate, or non-fluorinated sulfonate.

14. The photoresist composition of claim 7 wherein $Z^{31}$ contains a polymerizable moiety.

15. A photoresist composition that comprises an acid generator comprising a structure of Formula (IIa):

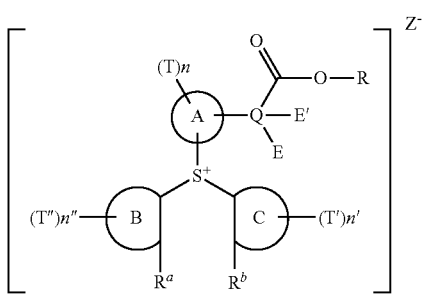

(IIa)

wherein Z is a counter anion;
R is —(CX'X")nC(=O)OR', wherein n is a positive integer, each X' and X" is independently a hydrogen or non-hydrogen substituent, and R' is a non-hydrogen substituent;
each T, each T' and each T" are the same or different non-hydrogen substituent, wherein either of T and T" or T and T' are capable of joining to form a ring;
n, n' and n" are 0, 1, 2, 3 or 4;
$R^a$ and $R^b$ are each H, or $R^a$ and $R^b$ taken together represent a chemical bond or a group capable of covalently linking B and C;
Q is a $C_1$-8 saturated or unsaturated alkylene group;
E and E' are each independently hydrogen or a non-hydrogen substituent, with at least one of E and E' being a non-hydrogen substituent; and
A, B, and C are each the same or different optionally substituted carbocyclic aryl or heteroaromatic groups.

16. A method for providing a photoresist relief image, comprising:
 a) applying a coating layer of a photoresist composition of claim 15 on a substrate; and
 b) exposing the photoresist composition layer to activating radiation and developing the exposed photoresist composition coating layer.

17. The photoresist composition of claim 15 wherein $R^a$ and $R^b$ are each H.

18. The photoresist composition of claim 15 wherein $R^a$ and $R^b$ taken together represent a chemical bond or a group capable of covalently linking B and C.

19. The photoresist composition of claim 15 wherein $Z^{31}$ is selected from the group consisting of carboxylate, sulfamate, or non-fluorinated sulfonate.

20. The photoresist composition of claim 15 wherein $Z^{31}$ contains a polymerizable moiety.

21. An acid generator that comprises a structure of Formula (VII):

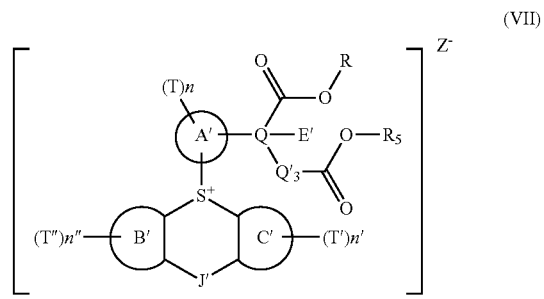

(VII)

wherein
Z is a counter anion;
R is hydrogen or a non-hydrogen substituent;
each T, each T' and each T" are the same or different non-hydrogen substituent, wherein either of T and T" or T and T' are capable of joining to form a ring;
n is 0, 1, 2, 3 or 4;
n' and n" are each independently 0, 1, 2, 3, 4 or 5;
E is hydrogen or a non-hydrogen substituent;
A', B', C' are each independently a $C_6$-$C_{36}$ aromatic, $C_5$-$C_{36}$ polyaromatic, or $C_5$-$C_{36}$ conjugated aromatic group;
J' represents no bond, a single chemical bond, or a group capable of covalently linking B' and C';
$R_5$ is hydrogen or a non-hydrogen substituent; and
$Q'_3$ is a $C_{1-8}$ alkylene group.

22. A photoresist composition that comprises an acid generator of claim 21.

23. A method for providing a photoresist relief image, comprising:
 a) applying a coating layer of a photoresist composition of claim 22 on a substrate; and
 b) exposing the photoresist composition layer to activating radiation and developing the exposed photoresist composition coating layer.

24. An acid generator that comprises a structure selected from the group consisting of:

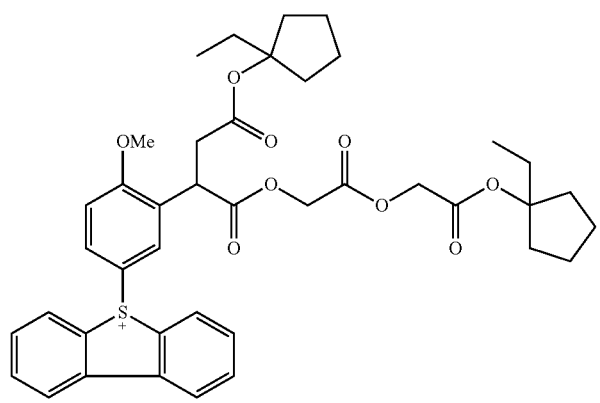

,

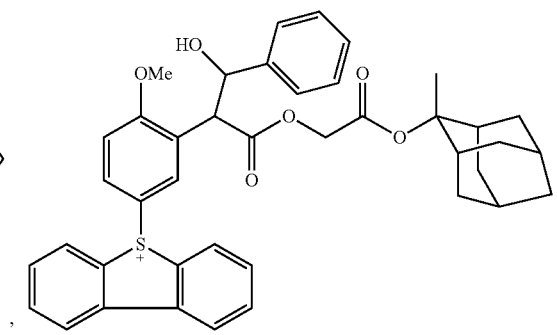

,

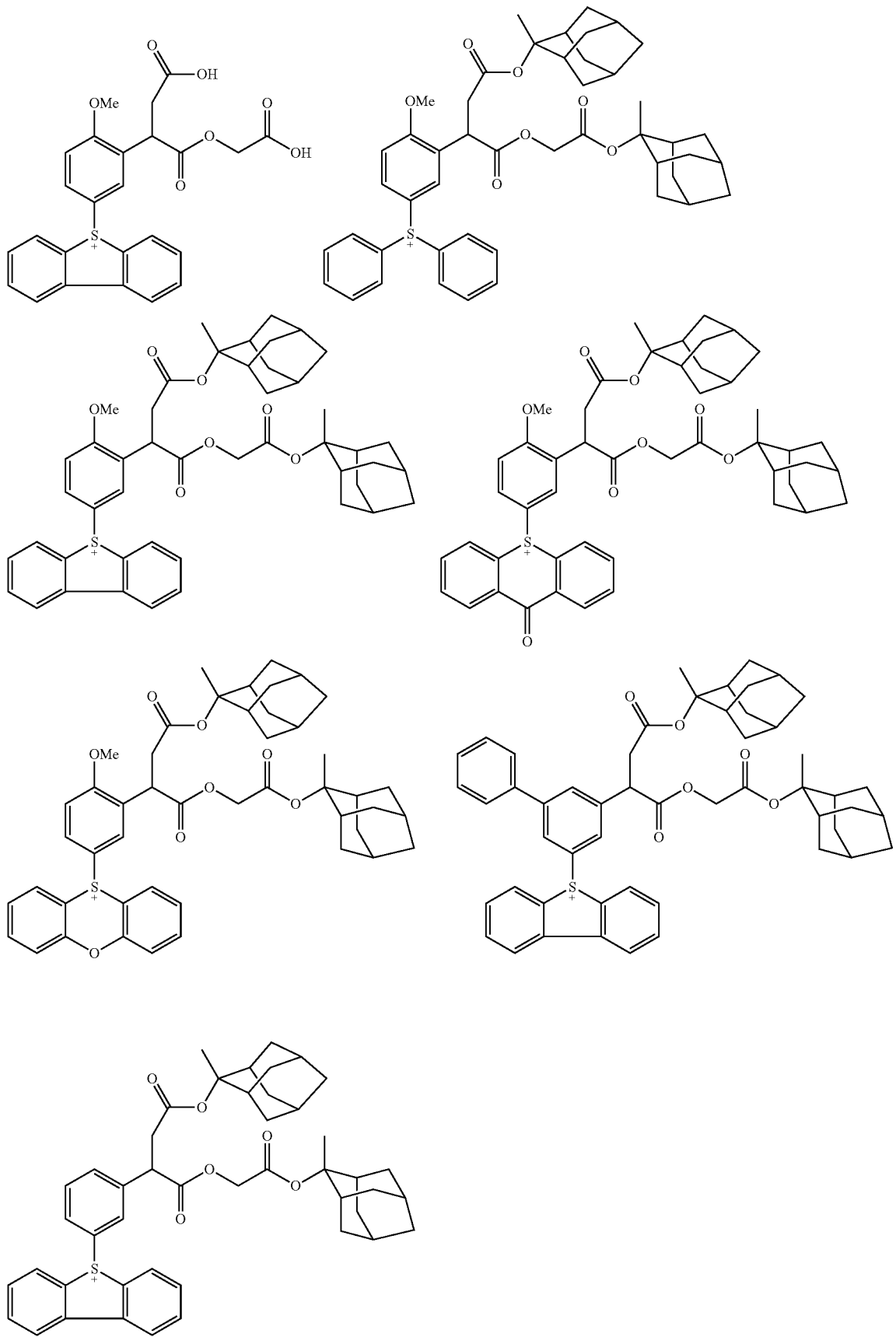

-continued
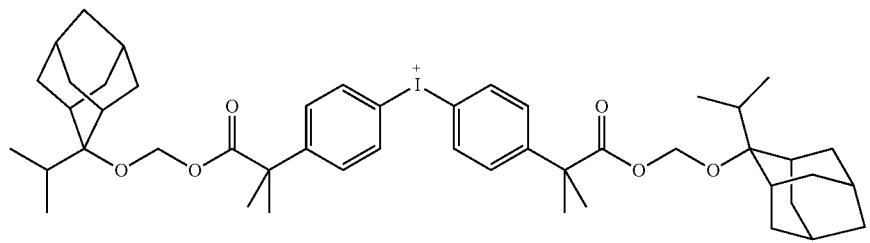
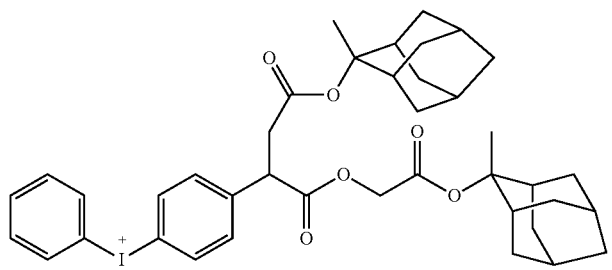
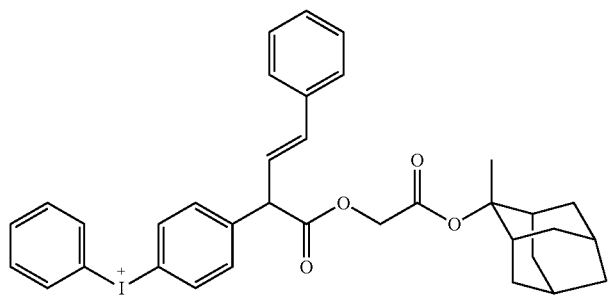
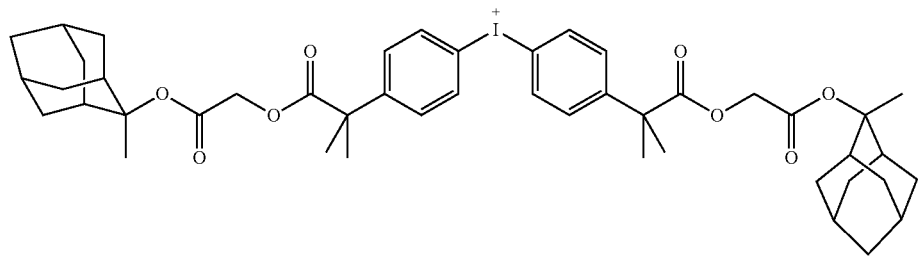
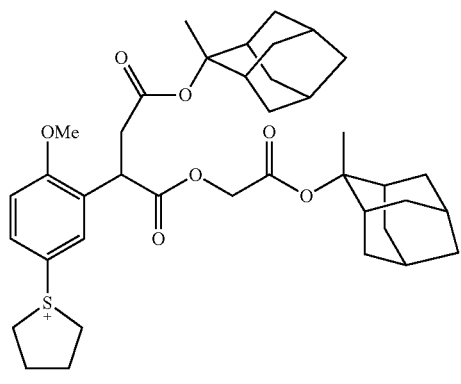
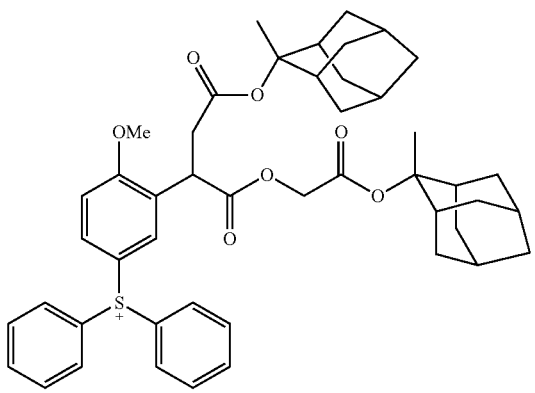

-continued
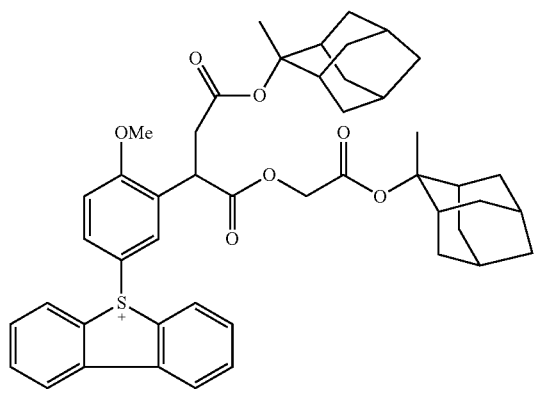
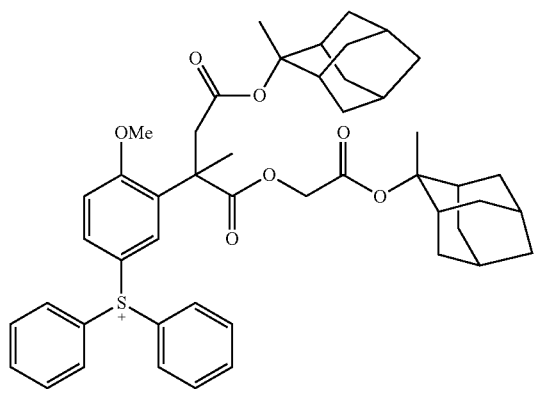
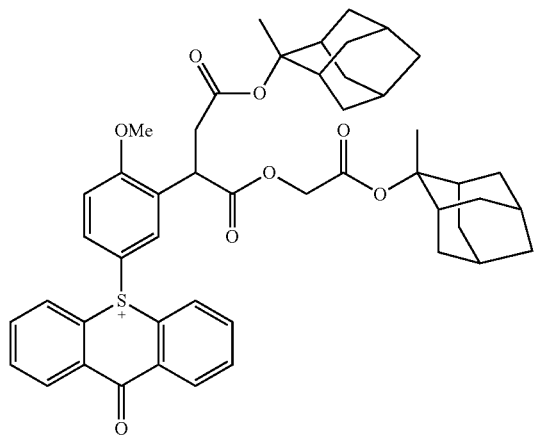
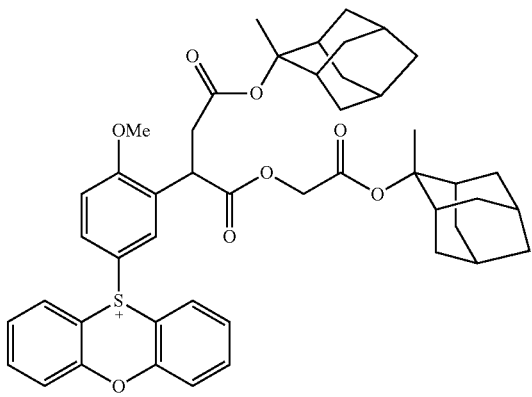
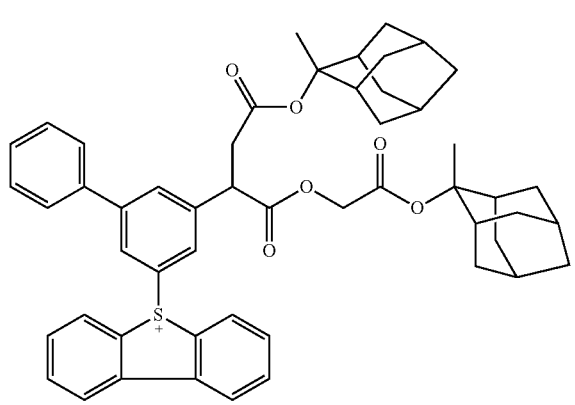
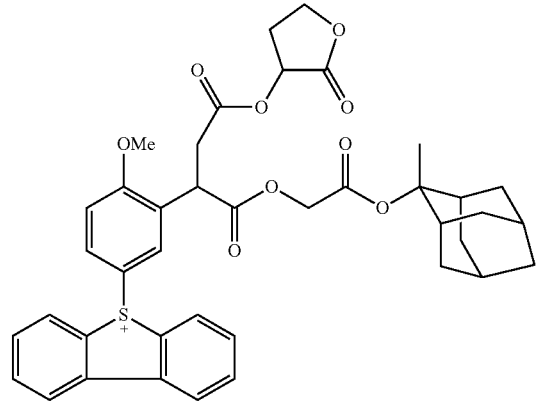
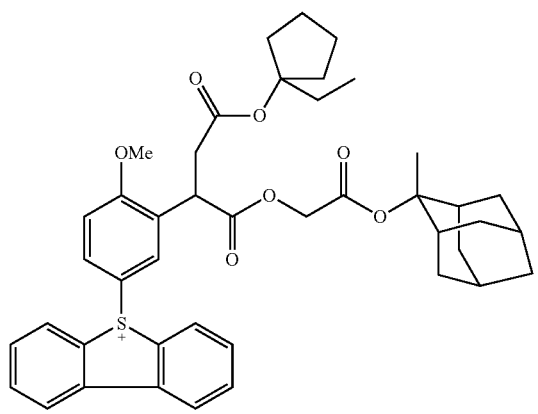
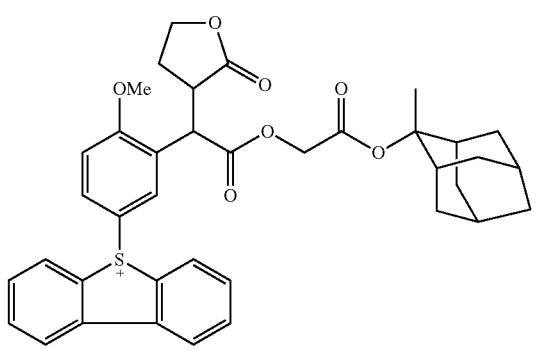

-continued
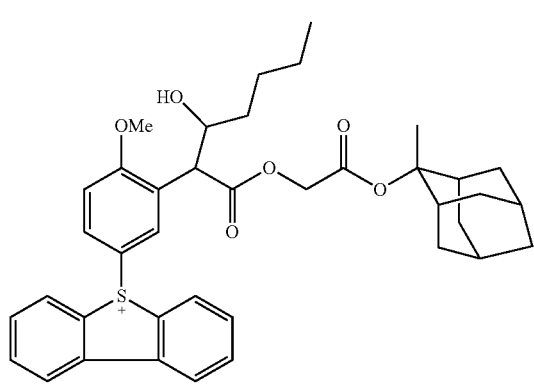
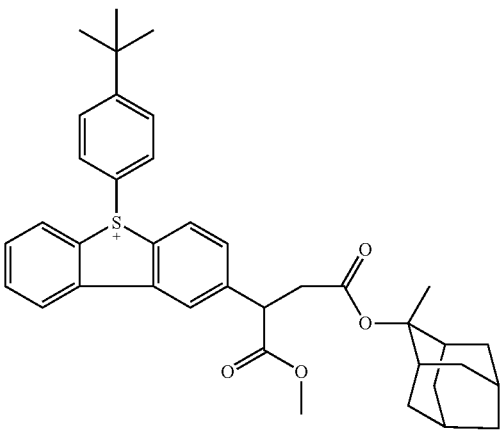
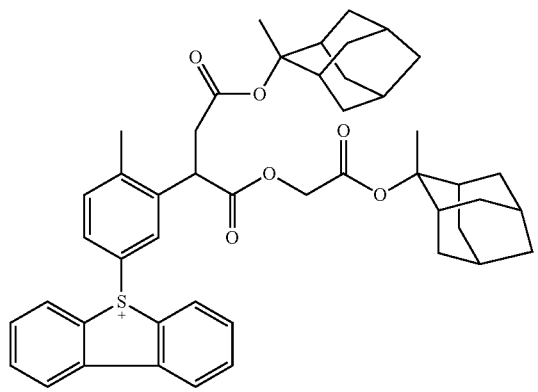
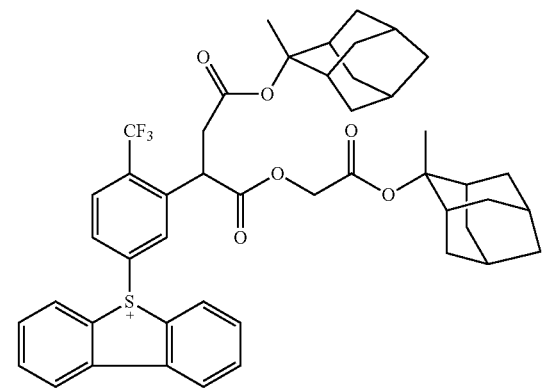
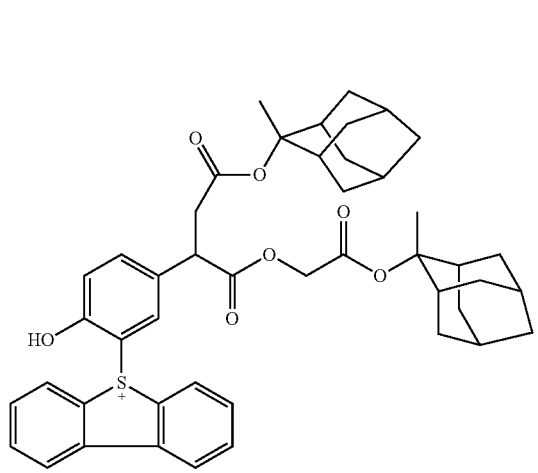
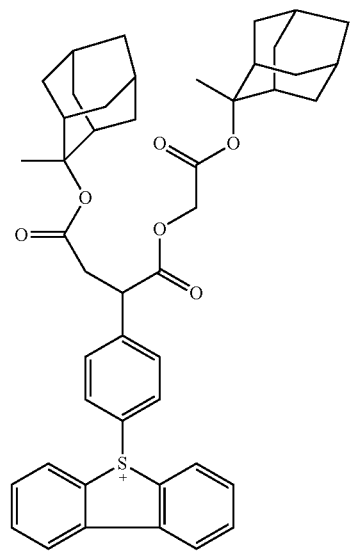
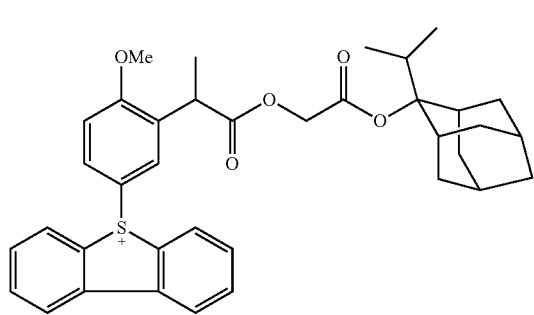
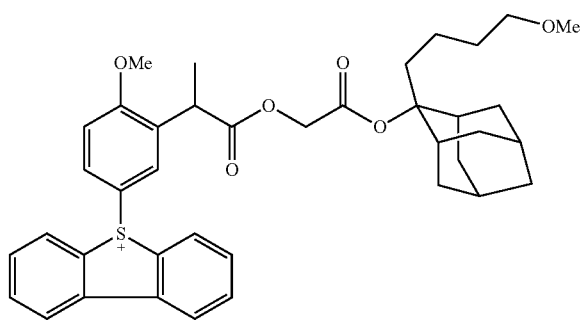

81 82
-continued
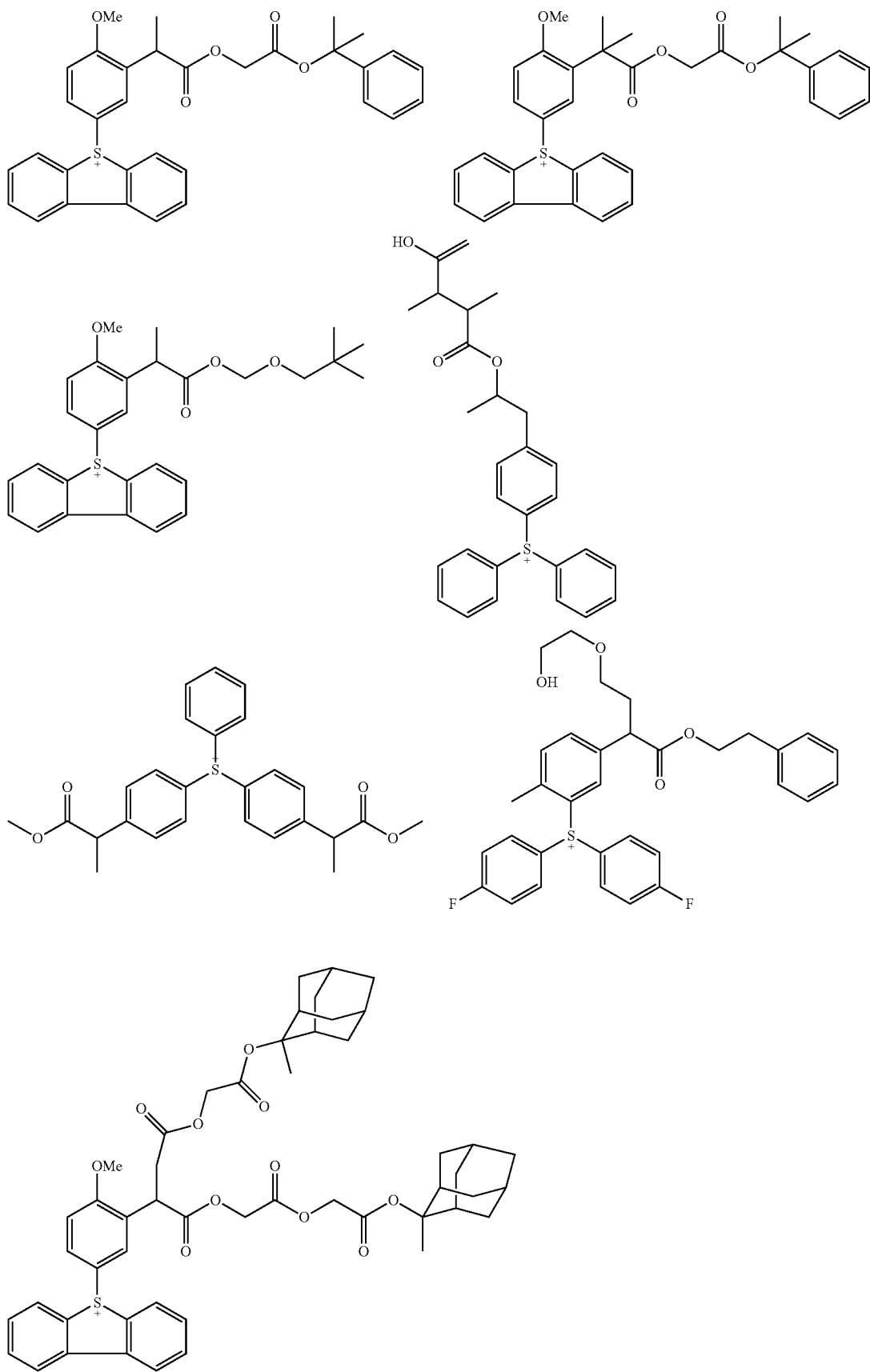

83
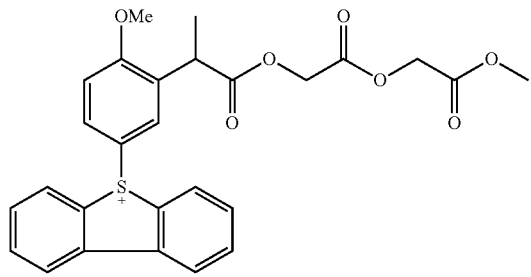
84
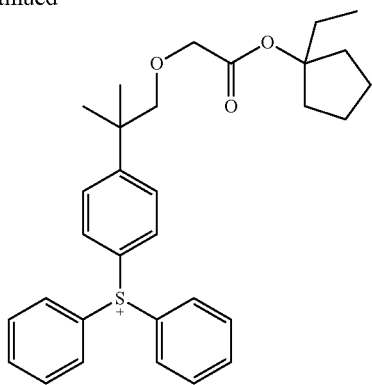
-continued
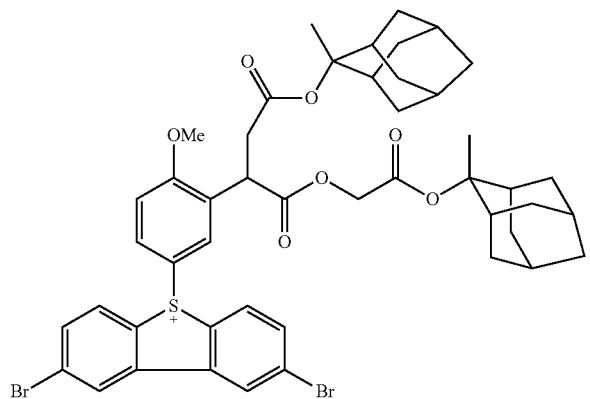
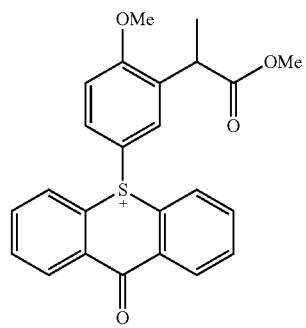
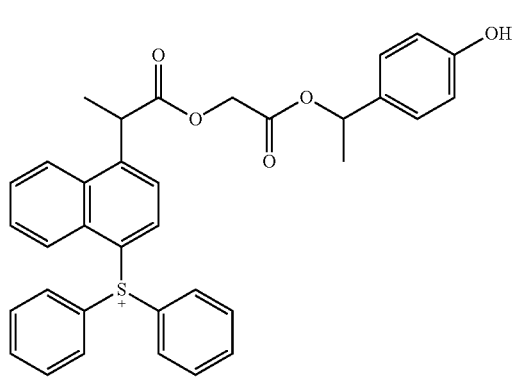
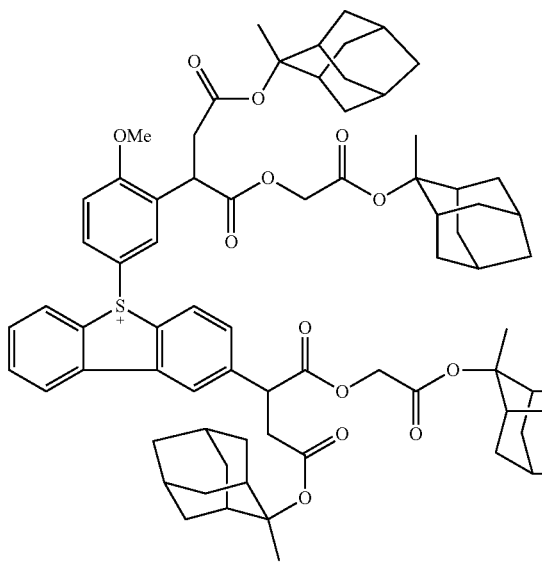
and -continued

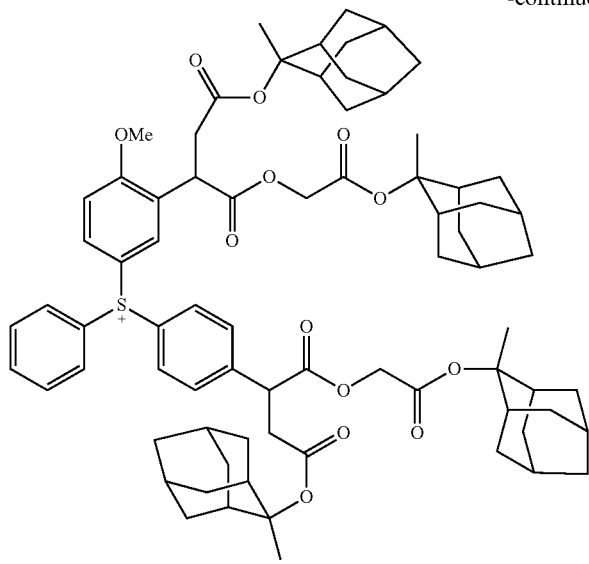

25. A photoresist composition that comprises an acid generator of claim 24.

26. A method for providing a photoresist relief image, comprising:
   a) applying a coating layer of a photoresist composition of claim 25 on a substrate; and
   b) exposing the photoresist composition layer to activating radiation and developing the exposed photoresist composition coating layer.

* * * * *